United States Patent [19]

Patchett et al.

[11] Patent Number: 4,617,301
[45] Date of Patent: Oct. 14, 1986

[54] SULFOXIDE AND SULFONE DERIVATIVES OF BICYCLIC LACTAMS AS ANTIHYPERTENSIVES

[75] Inventors: Arthur A. Patchett, Westfield; Matthew J. Wyvratt, Jr., Mountainside, both of N.J.

[73] Assignee: Merck & Co., Inc., Rahway, N.J.

[21] Appl. No.: 506,925

[22] Filed: Jun. 22, 1983

[51] Int. Cl.$^4$ ..................... A61K 31/55; C07D 513/04
[52] U.S. Cl. ..................................... 514/214; 540/521
[58] Field of Search .................. 260/239.3 B; 424/270

[56] References Cited

U.S. PATENT DOCUMENTS

| | | | |
|---|---|---|---|
| 3,334,091 | 8/1967 | Houlihan | 260/239.3 B |
| 4,052,511 | 10/1977 | Cushman et al. | 424/274 |
| 4,129,571 | 12/1978 | Ondetti et al. | 424/274 |
| 4,154,960 | 5/1979 | Ondetti et al. | 424/274 |
| 4,192,945 | 3/1980 | Ondetti et al. | 424/274 |
| 4,225,495 | 9/1980 | Ondetti et al. | 424/274 |
| 4,415,496 | 11/1983 | Harris et al. | 260/239.3 B |

OTHER PUBLICATIONS

Noller, "Chemistry of Organic Compounds", 2nd Edition (Saunders) (1957), pp. 272–291.
Derwent Abstract of German Pat. Appln. 2704-985, U.S. 657,605.
Derwent Abstract of German Pat. Appln. 2720-996, U.S. 685,605.
Derwent Abstract of German Pat. Appln. 2810-261, U.S. 776,792.
Abstract of ACS meeting of 9/11/78 entitled Superactive Analogs of the Angiotensin Converting Enzyme Inhibitor BPP$_{9a}$ Containing L-3,4-dehydroproline.
A. G. Schultz, J. Org. Chem., 45, 5008–9 (1980).

Primary Examiner—Robert T. Bond
Attorney, Agent, or Firm—Salvatore C. Mitri; Michael C. Sudol

[57] ABSTRACT

Sulfoxide and sulfone derivatives of bicyclic lactams are disclosed which are useful as converting enzyme inhibitors and as antihypertensives.

21 Claims, No Drawings

SULFOXIDE AND SULFONE DERIVATIVES OF BICYCLIC LACTAMS AS ANTIHYPERTENSIVES

BACKGROUND OF INVENTION

The invention in its broad aspects relates to sulfoxide and sulfone derivatives of bicyclic lactams which are useful as converting enzyme inhibitors and as antihypertensives. The compounds of this invention are represented by the following formula:

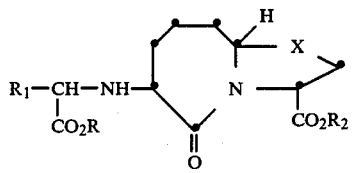

wherein:

X is SO or $SO_2$;

R and $R_2$ are independently hydrogen, loweralkyl, aryl, and aralkyl;

$R_1$ is hydrogen;

straight chain and branched alkyl, alkenyl, and alkynyl of from 1 to 12 carbon atoms (such as 3-methyl-1-butyl, 3,3-dimethylallyl, and the like);

cycloalkyl of 3 to 10 carbon atoms;

substituted lower alkyl wherein the substituent can be halo, hydroxy, carboxy, lower alkylthio, lower alkoxy, lower alkoxy carbonyl, lower aralkoxy carbonyl, amino, lower alkylamino, lower dialkylamino, or acylamino;

substituted lower alkyl having the formula $R_A(CH_2)_n$—Q—$(CH_2)_m$ wherein n is 0-2, m is 1-3, $R_A$ is aryl or heteroaryl optionally substituted by amino, lower dialkylamino, lower alkylamino, hydroxy, hydroxy loweralkyl, aminoloweralkyl, trihaloloweralkyl, cyano, nitro, sulfonamido, aroyl, lower alkyl, halo, dihalo, and lower alkoxy, and Q is O, S, N-$R_B$, CONR$_C$, NR$_C$CO, CH=CH wherein $R_B$ is hydrogen, loweralkyl, aryl, aralkyl, lower alkanoyl, or aroyl, and $R_C$ is hydrogen or lower alkyl;

aryl (such as phenyl, naphthyl or biphenyl);

substituted aryl wherein the substituent is lower alkyl, amino loweralkyl, loweralkoxy, aryloxy, aroyl, hydroxy, halo, or dihalo;

aralkyl or heteroaralkyl which include branched lower alkyl groups (such as 2,2-dibenzylethyl);

substituted aralkyl or substituted heteroaralkyl which include branched lower alkyl groups wherein the lower alkyl groups can be substituted by amino, acylamino, or hydroxyl and the aryl and heteroaryl groups can be substituted by halo, dihalo, loweralkyl, hydroxy, loweralkoxy, aryloxy, aroyl, arylthio, amino, amino lower alkyl, lower alkanoylamino, aroylamino, lower dialkylamino, lower alkylamino, hydroxy, hydroxy loweralkyl, trihalo loweralkyl, nitro, cyano, or sulfonamido; and, the pharmaceutically acceptable salts thereof.

The lower alkyl groups, except where noted otherwise, represented by any of the variables include straight and branched chain hydrocarbon radicals from one to six carbon atoms, for example, methyl, ethyl, propyl, isopropyl, butyl, isobutyl, t-butyl, pentyl, isopentyl, hexyl or vinyl, allyl, butenyl and the like. The aralkyl and heteroaralkyl groups represented by any of the above variables have from one to six carbon atoms in the alkyl portion thereof and include, for example, benzyl, phenethyl, 3,3-diphenylpropyl, 3-indolylmethyl, and the like. Halo means chloro, bromo, iodo or fluoro. Aryl and the prefix "ar" where they appear in any of the radicals, except where noted, have 5-6 ring atoms such as, for example, phenyl, naphthyl, or biphenyl. Aroyl includes benzoyl, 1-naphthoyl, and the like. Heteroaryl includes, for example, indolyl, thienyl, imidazolyl, furyl, benzimidazolyl, pyridyl, quinolinyl, isoquinolinyl, and benzothienyl. Acylamino refers to lower alkanoylamino and aroylamino groups such as, for example, acetylamino, benzoylamino, and the like. Hetero denotes one of the heteroatoms N, O or S.

Preferred are those compounds of Formula I wherein:

X is SO or $SO_2$;

R and $R_2$ are hydrogen, loweralkyl, aryl or aralkyl; and $R_1$ is alkyl of 1-10 carbon atoms which include branched, cyclic and unsaturated alkyl groups;

substituted loweralkyl wherein the substituent can be hydroxy, lower alkylthio, amino, alkylamino, lower dialkylamino, and acylamino;

substituted lower alkyl having the formula $R_A(CH_2)_n$—Q—$(CH_2)_m$—wherein n is 0-2, m is 1-3, $R_A$ is aryl or heteroaryl optionally substituted by alkyl, halo, dihalo, amino, cyano, hydroxy, or alkoxy, and Q is O, S, N—$R_B$, CONR$_C$, NR$_C$CO, or CH=CH wherein $R_B$ is hydrogen, lower alkyl, aralkyl, lower alkanoyl, or aroyl and $R_C$ is hydrogen or lower alkyl; aralkyl or heteroaralkyl which include branched lower alkyl groups;

substituted aralkyl or substituted heteroaralkyl which include branched lower alkyl groups wherein the lower alkyl substituents can be amino, acylamino, or hydroxy and the aryl and heteroaryl substituents can be lower alkyl, halo, dihalo, amino, cyano, hydroxy, lower alkoxy, amino loweralkyl, or hydroxyloweralkyl.

Still more preferred are those compounds of Formula I wherein:

X is SO or $SO_2$;

R and $R_2$ are independently hydrogen, loweralkyl, aryl, or aralkyl; and, $R_1$ is alkyl of 1-10 carbon atoms which include branched alkyl groups;

substituted lower alkyl wherein the substituent can be amino, acylamino, or lower alkylthio;

substituted lower alkyl having the formula $R_A(CH_2)_n$—Q—$(CH_2)_m$—wherein n is 0-1, m is 1-2, $R_A$ is phenyl optionally substituted by halo, dihalo, alkoxy, or cyano, and Q is O or S; aralkyl or heteroaralkyl;

substituted aralkyl or substituted heteroaralkyl wherein the aryl and heteroaryl substituents are halo, dihalo, cyano, hydroxy, hydroxy lower alkyl, amino, and amino lower alkyl.

Most preferred are compounds of Formula I wherein:

X is SO or $SO_2$;

R and $R_2$ are independently hydrogen, lower alkyl of 1 to 4 carbon atoms, phenyl, or benzyl; and, $R_1$ is alkyl of 1-8 carbon atoms which include branched alkyl groups;

substituted lower alkyl wherein the substituent can be amino or loweralkylthio; substituted lower alkyl having the formula $R_A(CH_2)_n$—Q—$(CH_2)_m$—wherein n is 0, m is 1, $R_A$ is phenyl, and Q is O or S; aralkyl wherein the aryl is phenyl or naphthyl and the alkyl group contains 1 to 3 carbon atoms, or heteroaralkyl wherein the heteroaryl group is indole, thiophene, imidazole, pyridine, quinoline or isoquinoline and the alkyl group contains 1 to 3 carbon atoms;

substituted aralkyl wherein the aryl is a phenyl group, the alkyl contains 1 to 3 carbon atoms, and the phenyl substituents can be halo, hydroxy, phenoxy, lower alkoxy, amino, or aminomethyl.

The preferred, more preferred and most preferred compounds also include the pharmaceutically acceptable salts thereof.

The products of Formula I can be prepared according to the methods described hereinbelow in Reaction Schemes I–IV wherein R, $R_1$ and $R_2$ are as defined above unless otherwise specified.

As shown in Reaction Scheme I below, preferred products of Formula I can be produced from bicyclic lactam II. Treatment of bicyclic lactam II in which the amine is protected as a hydrochloride salt with one equivalent of an oxidizing agent, such as m-chloroperoxybenzoic acid, produces compounds I' where X=SO. Since the sulfoxide center represents a new chiral center, two diastereomeric sulfoxides are possible. Reaction of II with an excess of oxidant affords compounds I'' where X=SO$_2$. Treatment of I' where X=SO with an excess of an oxidizing agent also affords compounds I'' where X=SO$_2$.

REACTION SCHEME I

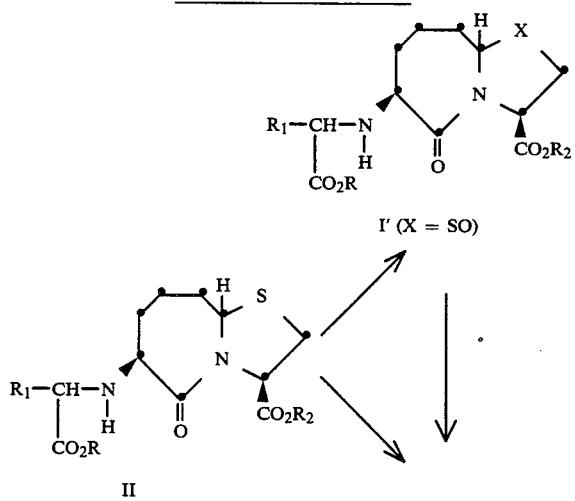

-continued
REACTION SCHEME I

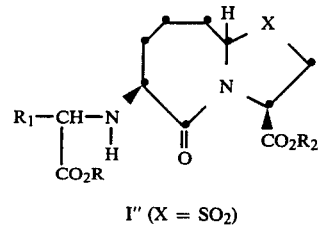

I'' (X = SO$_2$)

The preferred bicyclic lactam structure (II) can be produced according to the procedures disclosed in European Patent Application No. 82,102,330.6 which is incorporated herein by reference, or by the novel procedure illustrated in Reaction Scheme II below. In this new process, the known commercially available starting material, N$_\epsilon$-t-BOC-L-lysine (III) is first reacted with N-carbethoxyphthalimide and then with trifluoroacetic acid to produce IV. Condensation of IV with the known 4-formyl-1-methylpyridinium benzenesulfonate [T. F. Buckley, et al., *J. Am. Chem. Soc.*, 104, 4446–50 (1982)] produces a Schiff base which is equilibrated to V by the addition of base (1,8-diazabicyclo[5.4.0]undec-7-ene) (DBU). Addition of one equivalent of an ester of R-cysteine, hydrochloride to V forms a diastereomeric mixture of thiazolidines VI. Cyclization to the preferred bicyclic lactam diastereomers VIIa (S,R,R diastereomer) and VIIb (S,S,R diastereomer) (1:1 ratio) is achieved with N-ethoxycarbonyl-2-ethoxy-1,2-dihydroquinoline (EEDQ) or N-isobutoxycarbonyl-2-isobutoxy-1,2-dihydroquinoline (IIDQ). Diastereomers VIIa and VIIb can be separated by column chromatography.

The more preferred diastereomer VIIa can also be obtained by treating VIIb or a mixture of VIIa and VIIb with a strong acid, such as p-toluenesulfonic acid or Amberlyst 15 resin in benzene at reflux. This establishes an equilibrium between VIIb and VIIa in which VIIa predominates by a large margin. (Weight ratio of VIIa:VIIb is about 96:4.) Treatment of VIIa and VIIb with hydrazine gives the amino lactams VIIIa and VIIIb, respectively. Lactam VIIIb can be equilibrated to VIIIa by a similar acid treatment such as, for example, with trifluoroacetic acid. The ester group can then be removed with dilute alkali or, in the case $R_2=CH_2Ph$, by hydrogenolysis to yield the acids ($R_2=H$) of VIIIa and VIIIb.

REACTION SCHEME II

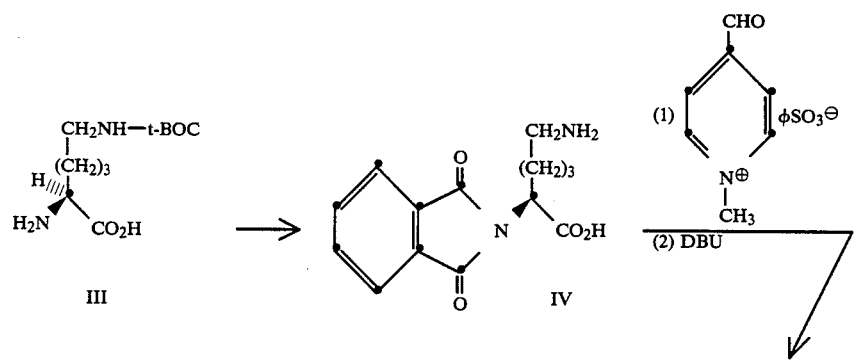

-continued
REACTION SCHEME II

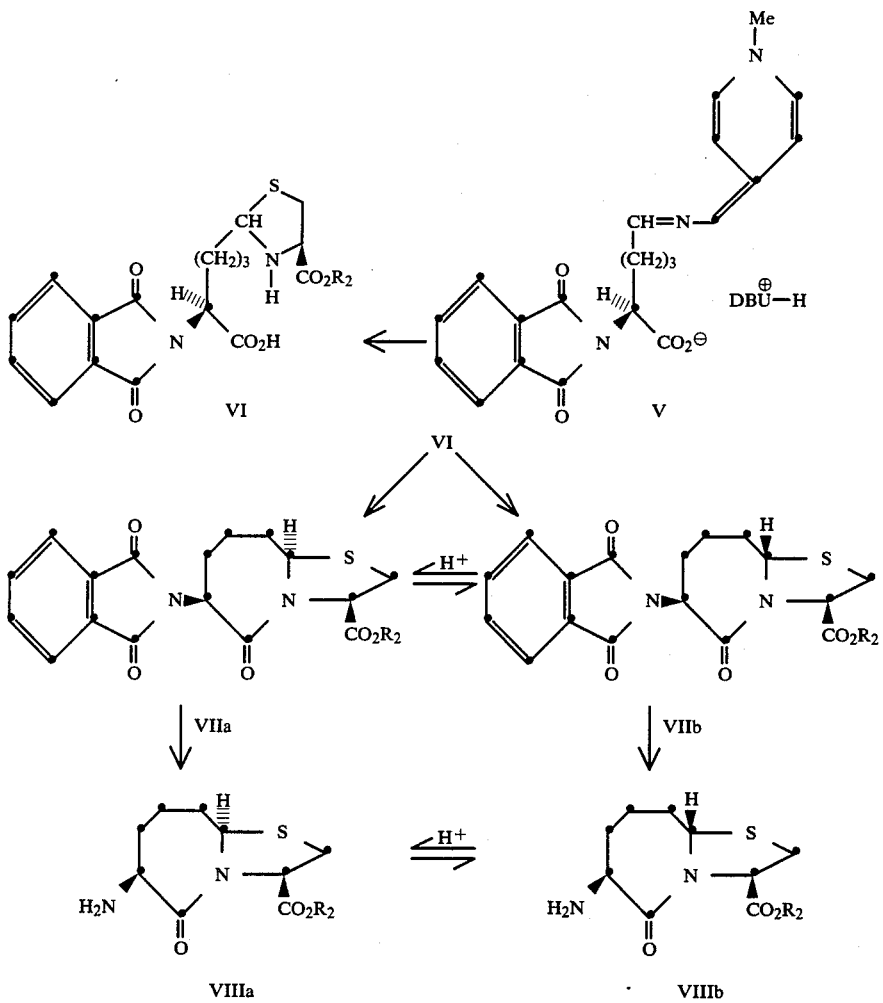

As summarized in Reaction Scheme III below, products of Formula II can be prepared from the diastereomeric mixture of amino cyclic lactams VIII or from diastereomerically pure compounds VIIIa and VIIIb by reductive alkylation of these intermediates with α-keto acids or α-keto esters IX. In these alkylations, one typically uses sodium cyanoborohydride under neutral conditions, but it is also possible to employ hydrides bearing optically active ligands or sterically bulky ligands selected to improve the stereochemical control in these reductions. These reductive alkylations can also be achieved by catalytic hydrogenation over 10% palladium on carbon or other suitable catalysts.

As also summarized in Reaction Scheme III, products of Formula I can be prepared from the diastereomeric mixture of IIa, IIb or from diastereomerically pure IIa or IIb. In general, the amine functionality is protected as an acid salt, such as its hydrochloride salt, during the oxidation of IIa/b to products of Formula Ia or Ib where X=SO or $SO_2$. In the case where X=SO, a new asymmetric center is created at the sulfur and, consequently, diastereomers at this center are possible, in which case they can be employed as a mixture of diastereomers or separated and used as pure diastereomers.

REACTION SCHEME III

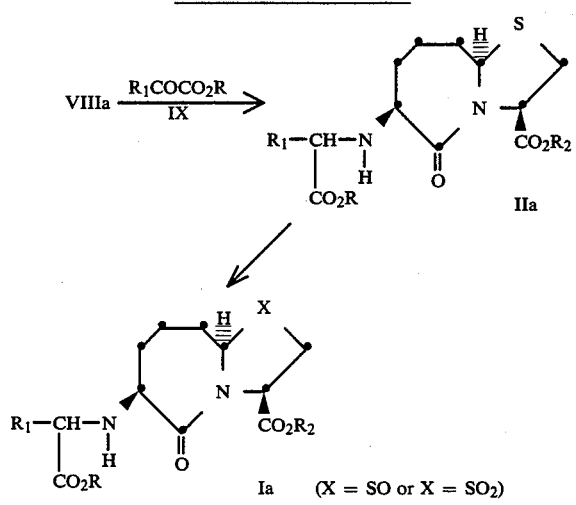

-continued
REACTION SCHEME III

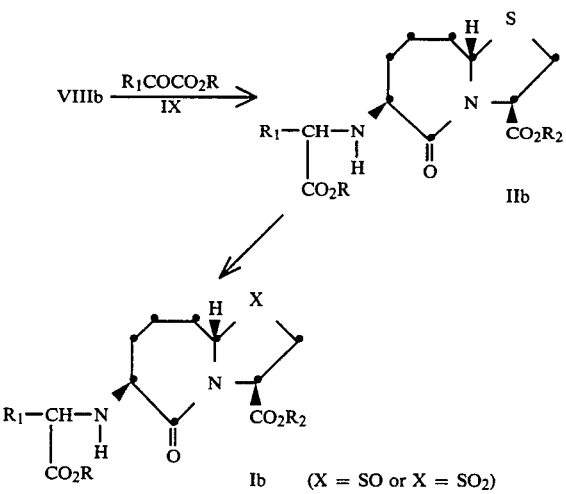

Ib  (X = SO or X = SO$_2$)

In Reaction Scheme IV which follows, an alternative route to compounds of Formula I is shown which involves a variation in the sequence of the reactions utilized in Reaction Schemes II and III. In Reaction Scheme IV, oxidation of the sulfide in intermediates VII or VIII is accomplished with removal of protecting groups, if any, prior to the reductive alkylation reaction with α-keto acids or α-keto esters, IX. By this procedure, R$_1$ side chains containing functionality susceptible to oxidation (for example, when R$_1$ is φCH$_2$SCH$_2$—) can be introduced to give products of Formula I.

REACTION SCHEME IV

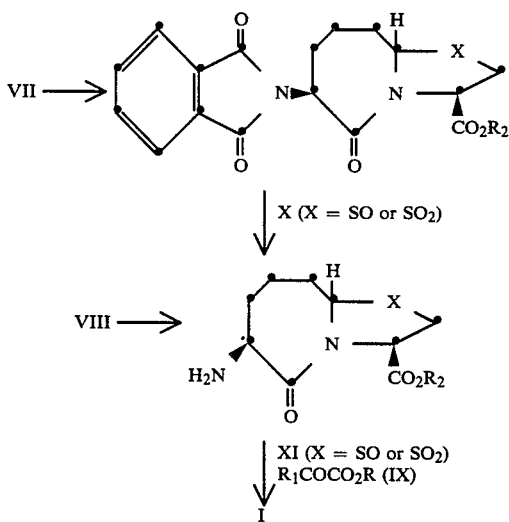

Intermediate VIII has three asymmetric carbon atoms: one bears the NH$_2$ group; another is that bearing the hydrogen at the ring juncture; and, a third is that bearing the CO$_2$R$_2$ group. The preferred absolute configuration at these centers are 6(S), 9a(R), 3(R)(VIIIa) and 6(S), 9a(S), 3(R)(VIIIb). When X=SO, intermediate XI has, in addition to the three asymmetric centers described for VIII, a fourth center at the sulfur which can have R and S absolute configurations.

In Formula I compounds, the carbon atom bearing R$_1$ is also asymmetric (R$_1$≠H). Both isomers in this position have some biological activity, although the natural L-aminoacid configuration is preferred. In most cases, the absolute configuration at this center is designated (S).

Preferred diastereomers are isolated by chromatography or crystallization of intermediates or the end products or their salts. One can also resolve intermediates by the use of optically active salts or bases. Finally, if desired, compounds of this invention can also be employed as a mixture of their enantiomers or diastereomers.

The α-keto acids and α-keto esters IX utilized in the process of the invention are known in the art or can be made by numerous, known methods. For example, synthons such as

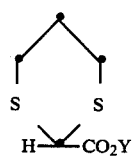

can be converted to o-keto acids or esters using methods involving alkylation followed by hydrolysis as described in the literature. An excellent method involves the reaction of Grignard reagents R$_1$MgX with ClCO-CO$_2$Y or YO$_2$CCO$_2$Y. Another method involves condensing substituted acetic acid esters with diethyl oxalate followed by hydrolytic decarboxylation under acidic conditions to obtain α-keto acids. Carefully controlled acid hydrolysis in alcohol of acyl cyanides, which are prepared from acid chlorides and cuprous cyanide, also proves to be a viable synthetic route to α-keto esters. Nucleophilic displacement reactions on chloro or bromo pyruvic acid (ester) can also be used to produce a variety of interesting α-keto acids (esters). In these formulae, Y is a group such as loweralkyl or benzyl and protecting groups are employed as necessary in the R$_1$ group if interfering functionality is present.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases e.g., dicyclohexylamine salts, N-methyl-D-glucamine, salts with amino acids like arginine, lysine and the like. Also salts with organic and inorganic acids may be prepared, e.g., HCl, HBr, H$_2$SO$_4$, H$_3$PO$_4$, methanesulfonic, toluenesulfonic, maleic, fumaric, camphorsulfonic. The non-toxic physiologically acceptable salts are preferred, although other salts are also useful, e.g., in isolating or purifying the product.

The salts may be formed by conventional means as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

The compounds of this invention inhibit angiotensin converting enzyme and thus block conversion of the decapeptide angiotensin I to angiotensin II. Angiotensin II is a potent pressor substance. Thus, blood-pressure lowering can result from inhibition of its biosynthesis especially in animals and humans whose hypertension is angiotensin II related. Furthermore, converting enzyme degrades the vasodepressor substance, bradykinin. Therefore, inhibitors of angiotensin converting enzyme may lower blood-pressure also by potentiation of bradykinin. Although the relative importance of these and other possible mechanisms remains to be established, inhibitors of angiotensin converting enzyme are effective antihypertensive agents in a variety of animal models and are useful clinically, for example, in many human patients with renovascular, malignant and essential hypertension. See, for example, D. W. Cushman et al., *Biochemistry* 16, 5484 (1977).

The evaluation of converting enzyme inhibitors is guided by in vitro enzyme inhibition assays. For example, a useful method is that of Y. Piquilloud, A. Reinharz and M. Roth, *Biochem. Biophys. Acta*, 206, 136 (1970) in which the hydrolysis of carbobenzyloxyphenylalanylhistidinylleucine is measured. In vivo evaluations may be made, for example, in normotensive rats challenged with angiotensin I by the technique of J.R. Weeks and J.A. Jones, *Proc. Soc. Exp. Biol. Med.*, 104, 646 (1960) or in a high renin rat model such as that of S. Koletsky et al., *Proc. Soc. Exp. Biol. Med.* 125, 96 (1967).

Thus, the compounds of this invention are useful as antihypertensives in treating hypertensive mammals, including humans, and they can be utilized to achieve the reduction of blood pressure by formulating in compositions such as tablets, capsules or elixirs for oral administration or in sterile solutions or suspensions for parenteral administration. The compounds of this invention can be administered to patients in need of such treatment in a dosage range of 0.5 to 100 mg per patient generally given several times, thus giving a total daily dose of from 0.5 to 400 mg per day. The dose will vary depending on severity of disease, weight of patient and other factors which a person skilled in the art will recognize.

It is often advantageous to administer compounds of this invention in combination with other antihypertensives and/or diuretics. For example, the compounds of this invention can be given in combination with such compounds as amiloride, atenolol, bendroflumethiazide, chlorothalidone, chlorothiazide, clonidine, cryptenamine acetate and cryptenamine tannates, deserpidine, diazoxide, ethacrynic acid, furosemide, guanethidene sulfate, hydralazine hydrochloride, hydrochlorothiazide, hydroflumethiazide, metolazone, metoprolol tartate, methyclothiazide, methyldopa, methyldopate hydrochloride, minoxidil, (S)-1-{[2-(3,4-dimethoxyphenyl)ethyl]amino}-3-{[4-(2-thienyl)-1H-imidazol-2-yl]phenox}-2-propanol, polythiazide, the pivaloyloxyethyl ester of methyldopa, indacrinone and variable ratios of its enantiomers, nifedipine, verapamil, diltiazam, flumethiazide, bendroflumethiazide, atenolol, (+)-4-{3-}-[2-(1-hydroxycyclohexyl)ethyl]-4-oxo-2-thiazolidinyl{propy}benzoic acid, bumetanide, prazosin, propranolol, *rauwolfia serpentina*, rescinnamine, reserpine, spironolactone, timolol, trichlormethiazide, benzthiazide, quinethazone, tricrynafan, triamterene, acetazolamide, aminophylline, cyclothiazide, merethoxylline procaine, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the antihypertensives of this invention effective clinically in the 0.5-100 milligrams per day range can be effectively combined at levels at the 0.1-100 milligrams per day range with the following compounds at the indicated per day dose range: hydrochlorothiazide (10-100 mg), timolol (5-60 mg), methyldopa (65-2000 mg), the pivaloyloxyethyl ester of methyldopa (30-1000 mg), indacrinone and variable ratios of its enantiomers (25-150 mg) and (+)-4-{3-[2-(1hydroxycyclohexyl)ethyl]-4-oxo-2-thiazolidinyl]propyl}-benzoic acid (10-100 mg).

In addition, the triple drug combinations of hydrochlorothiazide (10-100 mg) plus timolol (5-60 mg) plus converting enzyme inhibitor of this invention (0.5-100 mg) or hydrochlorothiazide (10-100 mg) plus amiloride (5-20 mg) plus converting enzyme inhibitor of this invention (0.5-100 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, the combinations shown above are formulated into pharmaceutical compositions as discussed below.

About 0.1 to 50 mg of a compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules, and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc. or a synthetic fatty vehicle like ethyl oleate or the like. Buffers, preservatives, antioxidants and the like can be incorporated as required.

The following examples are illustrative of the invention and constitute especially preferred embodiments. The preferred diastereomers of these examples are isolated by conventional column chromatography or fractional crystallization. Unless otherwise indicated, all temperatures are in degrees Celsius.

EXAMPLE 1

N$_\alpha$-Phthaloyl-L-lysine

Commercially obtained N$_\epsilon$-t-BOC-L-lysine (6.16 g, 0.025 mole) was suspended in 100 ml of an ethanol/water (1/3) mixture. Solid sodium carbonate (2.65 g, 0.025 mole) was added and the mixture was stirred for 3 hours. The ethanol was then removed under reduced pressure. To the aqueous residue, finely powdered N-carbethoxyphthalimide (5.48 g, 0.025 mole) was added and the mixture stirred for 1 hour. The reaction mixture was filtered, methylene chloride (100 ml) was added to the filtrate, and the pH of the aqueous layer was adjusted to pH 3.0 with 6N HCl (good stirring). Layers were separated and the aqueous layer further extracted with excess ethyl acetate. Combined organic phases were dried with MgSO$_4$ and concentrated, wt. 10.9 g.

To this residue, 50 ml of trifluoroacetic acid (TFA) was added with external cooling. The reaction mixture was then stirred for 2.5 hours at room temperature. The mixture was concentrated under reduced pressure and added to a Dowex 50-X2 column (160 ml, acid cycle). The column was initially eluted with methanol/water (1/1), then water, and finally with 4% pyridine/water to recover product. The appropriate fractions were concentrated and then freeze-dried, wt. 5.35 g. TLC on silica [1:1:1:1 ethyl acetate:n-butanol:water:acetic acid] indicated a single spot, R$_f$=0.52 (ninhydrin). The $^1$H NMR spectrum is consistent with the structure; $[\alpha]_D^{25°} = -30.5°$ (C=1.5, H$_2$O).

Anal. Calc'd. for C$_{14}$H$_{16}$N$_2$O$_4$-H$_2$O: C, 57.13; H, 6.16; N, 9.52. Found: C, 57.28; H, 5.90; N, 9.57.

EXAMPLE 2

Methyl 2-(4'(S)-carboxy-4'-phthalimidobutyl)-4(R)-thiazolidinecarboxylate

N$_\alpha$-Phthaloyl-L-lysine (8.57 g, 0.029 mole) and 4-formyl-1-methylpyridinium benzenesulfonate (8.13 g, 0.029 mole) were dissolved in 150 ml of dimethylformamide (dried over 4A molecular sieves). After thirty minutes, 1,8-diazabicyclo[5.4.0]undec7-ene (DBU, 9.06 ml, 0.058 mol) was added. The dark reaction mixture was stirred for 5 minutes at which point the hydrochloride salt of L-cysteine methyl ester (5.0 g, 0.029 mole) was added. The reaction mixture was stirred for two hours. The mixture was cooled with an ice bath and then treated with 300 ml of an aqueous solution of HCl (pH 1.7). Chloroform (130 ml) was added and the aqueous layer adjusted with 0.5M HCL to a pH of 4.4. The layers were separated and the aqueous layer further extracted with CHCl$_3$ (4×80 ml). The combined organic layers were back-washed with water (1×50 ml) and then concentrated under reduced pressure. The residue was dissolved in 200 ml of ethyl acetate and filtered through a celite pad. The filtrate was concentrated to afford a foam, 2.73 g. TLC on silica [4:1 ethyl acetate:acetic acid] indicated a major spot with R$_f$=0.75. Mass spectrum shows a molecular ion at 392. The $^1$H NMR spectrum indicates a 2:1 mixture of diastereomers: (200 MHz, CDCl$_3$) δ1.3–2.36 (m, 6H), 2.78–3.02 (m, 1H), 3.17–3.32 (m, 1H), 3.76, 3.78 (2s, 3H), 3.85 (dd, major diastereomer), 4.12 (t, minor), 4.45 (t, major), 4.60 (t, minor), 4.88 (m, major and minor), 5.32 (br s, active hydrogens), 7.76 (m, 2H), 7.88 (m, 2H).

EXAMPLE 3

Methyl [3R-[3α-6α-9aα]]-6-phthalimidooctahydro-5-oxo-thiazolo[3,2-a]azepine-3-carboxylate and methyl [3R-[3α,6α,9aβ]]-6-phthalimidooctahydro-5-oxo-thiazolo[3,2-a]azepine-3-carboxylate The mixture of diastereomeric thiazolidines (2.72 g, 6.93 mmole) obtained in Example 2 and 2.06 g of N-ethoxycarbonyl-2-ethoxy-1,2-dihydroquinoline (EEDQ) were dissolved in 90 ml of dry tetrahydrofuran. The reaction mixture was stirred under nitrogen for 3 days. The mixture was concentrated to dryness. The residue was dissolved in ethyl acetate (150 ml) and washed with 0.5N HCl (2×30 ml), 5% NaHCO$_3$ solution (30 ml), water (20 ml), and brine (30 ml). The solution was dried with sodium sulfate and then evaporated to give 2.21 g of crude product. Chromatography on silica gel (1:1 ethyl acetate:hexanes) gave 1.74 g of a 1:1 diastereomeric mixture. The diastereomers were separated on a Whatman ODS-3 reverse phase column (HPLC) using a 70:30 water-acetonitrile mixture as eluant.

The first component eluted from the column was methyl [3R-(3α,6α,9aα)]-6-phthalimidooctahydro5-oxothiazolo-[3,2-a]azepine-3-carboxylate (9a(S) isomer). Recrystallization from ethyl acetate/hexane afforded fine white needles, m.p. 159.5°–61°; $[\alpha]_D^{25°} = -202.1°$ (CHCl$_3$); 300 MHz $^1$H NMR(CDCl$_3$) δ1.99 (m, 3H), 2.29 (m, 2H), 2.94 (m, H), 3.27 (½ ABq, J$_{AB}$=12Hz, ΔV$_{AB}$=34, J$_{AX}$=7Hz, 1H), 3.16 (½ABq, J$_{AB}$=12 Hz, ΔV$_{AB}$=34, J$_{BX}$=7 Hz, 1H), 3.75 (s, 3H), 5.01 (d, J=12 Hz, H), 5.21 (t, J=7 Hz, 1H), 5.27 (dd, J=9.5 Hz, J=4 Hz, 1H), 7.75 (m, 2H), 7.88 (m, 2H); I.R. (KBr): 1710 and 1650 cm$^{-1}$.

Anal. Calc'd. for C$_{18}$H$_{18}$N$_2$O$_5$S: C, 57.74; H, 4.84; N, 7.48; S, 8.57.

Found: C, 57.70; H, 4.87; N, 7.41; S, 8.45.

The second component eluted from the column was methyl [3R-(3α,6α,9aβ)]-6-phthalimidooctahydro-5-oxothiazolo[3,2-a]azepine-3-carboxylate (9a(R) isomer, configuration determined by X-ray analysis). Recrystallization from ethyl acetate/hexane produced fine needles, m.p. 157°–157.5°; $[\alpha]_D^{25°} = -32.2°$ (CHCl$_3$); 300 MHz $^1$H NMR (CDCl$_3$)δ1.75–2.26 (m, 5H), 2.85 (q, J=12 Hz, 1H)), 3.22 (½ABq, J$_{AB}$=12 Hz, ΔV$_{AB}$=21.7; J$_{AX}$=6.5 Hz , 1H), 3.29 (½ABq, J$_{AB}$=12 Hz, ΔV$_{AB}$=21.7, J$_{BX}$=2 Hz, 1H), 3.79 (s, 3H), 4.99 (d, J=12 Hz, 1H), 5.15 (d, J =10 Hz, 1H), 5.34 (dd, J$_{AX}$=6.5 Hz, J$_{BX}$=2 Hz, 1H), 7.74 (m,2H), 7.87 (m,2H); I.R. (KBr):1750, 1710, and 1640 cm$^{-1}$.

3 Anal Calc'd. for C$_{18}$H$_{18}$N$_2$O$_5$S: C, 57.74; H, 4.84; N, 7.48; S, 8.57. Found: C, 58.04; H, 4.90; N, 7.43; S, 8.62.

EXAMPLE 4

Acid-Catalyzed Epimerization of Methyl [3R-(3α,6α,9aα)]-6-phthalimidooctahydro-5-oxo-thiazolo-[3,2-a]azepine-3-carboxylate to Methyl [3R-(3α,6α,9aβ)]-6-phthalimidooctahydro-5-oxo-thiazolo-[3,2-a]azepine-3-carboxylate A solution of methyl [3R-(3α,6α,9aα)]-6-phthalimidooctahydro-5-oxothiazolo-[3,2-a]azepine-3-carboxylate (25 mg) and p-toluenesulfonic acid (57 mg) in 5 ml of benzene was heated to reflux for 5.5 hours with water removal (Dean-Stark trap) and under nitrogen. The solution was concentrated and the residue partitioned between CH$_2$Cl$_2$ and 5% NaHCO$_3$ solution. The organic layer was washed with a 5% NaHCO$_3$ solution and then water. The solution, after drying (Na$_2$SO$_4$), gave 21 mg of product. HPLC analysis (RP18 column) indicated a ratio of 95:3:2 of methyl [3R-(3α,6α,9aβ)]-6-phthalimido- octahydro-5-oxo-thiazolo-[3,2-a]azepine-3carboxylate to methyl [3R-(3α,6α,9aα)]-6-phthalimido-octahydro-5-oxo-thiazolo[3,2-a]azepine-3-carboxylate to unknown. The products can then be separated by preparative HPLC as described in Example 3 or by recrystallization. Alternatively, Amberlyst 15 (5-fold excess by weight) can be used as the acid catalyst.

EXAMPLE 5

Methyl [3R-(3α,6α,9aβ)]-6-aminooctahydro-5-oxothiazolo[3,2-a]azepine-3-carboxylate hydrochloride Methyl [3R-(3α,6α,9aβ)]-6-phthalimido- octahydro-5-oxothiazolo[3,2-a]azepine-3-carboxylate (259 mg) was dissolved in 15 ml of absolute ethanol with gentle heating. Hydrazine hydrate (0.037 ml) was added and the mixture stirred at room temperature for 4 days under nitrogen. After concentration under vacuum to dryness, the residue was treated with 20 ml of 0.5M HCl at 0° for 3 hours. The precipitated phthalhydrazide was filtered off and the filtrate freeze-dried to yield 220 mg of product. Tlc on silica (1:1:1:1 ethyl acetate:n-butanol:water:acetic acid) indicated a single spot by ninhydrin, R$_f$=0.63. 'H NMR (200 MHz, CD$_3$OD)δ1.8–2.18 (m, 6H), 3.30 (2H), 3.77 (s, 3H), 4.26 (d, J=9 Hz, 1H), 5.17 (dd, J=7 Hz, J=3.5 Hz, 1H), 5.25 (t, J=4.5 Hz, 1H); exact mass measurement (free base), Obs. 244.0878, calc'd. 244.0881.

EXAMPLE 6

Methyl [3R-(3α,6α,9aα)]-6-aminooctahydro-5- c oxothiazolo[3,2-a]azepine-3-carboxylate Methyl [3R-(3α,6α,9aα)-6-phthalimidooctahydro-5-oxothiazolo[3,2-a]azepine-3-carboxylate (1.25 g) was dissolved in 80 ml of absolute ethanol with gentle heating. Hydrazine hydrate (0.178 ml) was added and the mixture stirred at room temperature for 4 days under nitrogen. The reaction mixture was concentrated and the residue dried under vacuum to remove trace amounts of hydrazine. The residue was treated with 0.5M HCl (85 ml) at 0° for 3 hours. The precipitated phthalhydrazide (495 mg) was collected. The filtrate was neutralized with 1M NaOH to pH 10.0 and extracted with CH$_2$Cl$_2$. Concentration afforded the amino ester, 0.8 g. Exact mass measurement: obs., 244.0880; calc'd., 244.0881. 'H NMR (200 MHz, CDCl$_3$) 1.58 (br s, 2H, NH$_2$), 1.66–2.20 (br m, 6H), 3.11 (½ABq, J$_{AB}$=13 Hz, ΔV$_{AB}$=35, J$_{AX}$=4 Hz, 1H), 3.29 (½ABq, J$_{AB}$=13 Hz, ΔV$_{AB}$=35, J$_{BX}$=7 Hz, 1H), 3.76 (s, 3H), 3.87 (m, 1H), 5.23 (dd, J=7 Hz, J=4 Hz, 1H), 5.55 (d, J=10 Hz, 1H).

EXAMPLE 7

Methyl [3R-(3α,6α,9aβ)]-6-aminooctahydro-5-oxothiazolo[3,2-a]azepine-3-carboxylate A mixture of (~1:1) of methyl [3R-(3R-(3α,6α,9aβ)]-6-aminooctahydro-5-oxothiazolo[3,2-a]-azepine-3-carboxylate hydrochloride and methyl [3R-(3α,6α,9aα)]-6-aminooctahydro-5-oxothiazolo[3,2-a]-azepine-3-carboxylate hydrochloride (1.30 g) in 65 ml of trifluoroacetic acid was heated at reflux under nitrogen for 20 hours. The reaction mixture was concentrated in vacuo. Analysis of the 'H NMR spectrum (200 MHz) of this product indicated the near complete conversion (>95%) of the mixture into methyl [3R-(3α,6α,9aβ)]-6-aminooctahydro-5-oxothiazolo[3,2-a]-azepine-3-carboxylate.

EXAMPLE 8

[3R-(3α,6α,9aβ)]-6-Aminooctahydro-5-oxo-thiazolo[3,2-a]-azepine-3-carboxylic acid Methyl [3R-(3α,6α,9aβ)]-6-aminooctahydro-5oxo-thiazolo[3,2-a]-azepine-3-carboxylate (220 mg) was dissolved in 5 ml of CH$_3$OH and treated with 4.3 ml of 1M NaOH at room temperature overnight. The reaction mixture was absorbed on 15 ml of strong acid ion-exchange resin and eluted with 3% pyridine in water to yield 133 mg of product. Tlc on silica [1:1:1:1 ethyl acetate:n-butanol:water:acetic acid] indicated a single spot at R$_f$=0.56. Recrystallized from methanol, m.p. 208°–210° (dec); [α]$_D^{25°}$=−84.5° (c=1.58, 1N HCl); 'H NMR (200 MHz, D$_2$O)δ2.02 (m, 6H), 3.27 (d, J=5 Hz, 2H), 4.32 (m, 1H), 4.97 (t, J=5 Hz, 1H), 5.16 (m, 1H).

Anal. Calc'd. for C$_9$H$_{14}$N$_2$O$_3$S: C, 46.94; H, 6.13; N, 12.17; S, 13.93. Found: C, 46.66; H, 6.34; N, 12.01; S, 13.69.

EXAMPLE 9

[3R-(3α,6α,9aα)]-6-Aminooctahydro-5-oxo-thiazolo[3,2-a]- azepine-3-carboxylic acid Methyl [3R-(3α,6α,9aα)]-6-aminooctahydro-5oxo-thiazolo[3,2-a]-azepine-3-carboxylate (629 mg) was dissolved in 4 ml of methanol and treated with 3.9 ml of 1M NaOH solution. The reaction mixture was stirred overnight at room temperature under nitrogen and then absorbed on strong acid ion-exchange resin. Elution with 3% pyridine in water permitted the recovery of product, 530 mg. Tlc on silica [1:1:1:1 ethyl acetate:n-butanol:water:acetic acid] indicated a single component, R$_f$=0.65. Recrystallized from water, m.p. 277° (dec); [α]$_D^{25°}$=−290.6° (C=0.43, 1N HCl); 'H NMR (200 MHz, D$_2$O)δ1.94–2.62 (m, 6H), 3.19 (½ABq, J$_{AB}$=12 Hz, ΔV$_{AB}$=57, J$_{AX}$=8 Hz, 1H), 3.45 (½ABq, J$_{AB}$=12 Hz, ΔV$_{AB}$=57, J$_{BX}$=7 Hz, 1H), 4.39 (d, J=11 Hz, 1H), 4.96 (m, 1H), 5.21 (d, J=9 Hz, 1H).

Anal. Calc'd for C$_9$H$_{14}$N$_2$O$_3$S: C, 46.94; H, 6.13; N, 12.17; S, 13.93. Found: C, 46.93; H, 6.18; N, 11.98; S, 13.80.

EXAMPLE 10

Benzyl [3R-(3α,6α,9aβ)]-6-aminooctahydro-5oxothiazolo[3,2-a]azepine-3-carboxylate

[3R-(3α,6α,9aβ)]-6-Aminooctahydro-5-oxo-thiazolo[3,2-a]azepine-3-carboxylic acid (205 mg) was suspended in 2.5 ml of benzyl alcohol and cooled with an ice bath. Thionyl chloride (0.26 ml) was added. After a few minutes, ice bath was removed and the mixture stirred at room temperature under nitrogen overnight. Ether (30 ml) was added and the resulting precipitate collected, wt. 313 mg. This material was suspended in 20 ml of H$_2$O and treated with 0.878 ml of 1M NaOH solution. After a few minutes, the mixture was extracted with CH$_2$Cl$_2$ (3×20 ml). The organic layers were dried (Na$_2$SO$_4$) and concentrated to give 193 mg of pure product. Tlc on silica [1:1:1:1 ethyl acetate:n-butanol:- water:acetic acid] indicated a single spot at $R_f=0.74$. Mass spectrum showed a molecular ion at 320 m/e. $^1$H NMR (200 MHz, CDCl$_3$)$\delta$1.40–2.02 (m, 6H), 1.68 (br s, —NH$_2$), 3.15 (m, 2H), 3.47 (d, J=11 Hz, 1H), 4.92 (d, J=8 Hz, 1H), 5.15 (s, 2H), 5.28 (dd, J=7 Hz, J =3Hz, 1H), 7.32 (s, 5H).

EXAMPLE 11

Benzyl [3R-(3α,6α,9aα)]-6-aminooctahydro-5-oxothiazolo[3,2-a]azepine-3-carboxylate

[3R-(3α,6α,9aα)]-6-Aminooctahydro-5-oxo-thiazolo[3,2-a]azepine-3-carboxylic acid can be suspended in benzyl alcohol at 0° and treated with thionyl chloride. The reaction mixture can be stirred overnight at room temperature and under an inert atmosphere. Ether can be added and the precipitate collected. The material can be suspended in water and then neutralized with one equivalent of base to afford, upon extraction, the desired compound.

EXAMPLE 12

Methyl [3R-[3α,6α(S*),9aβ]]-6-[(1-methoxycarbonyl-3-phenyl-propyl)amino]octahydro-5-oxothiazolo[3,2-a]azepine-3-carboxylate hydrochloride A solution of methyl [3R-[3α,6α,9aβ]]-6-aminooctahydro-5-oxothiazolo[3,2-a]azepine-3-carboxylate hydrochloride (414 mg) in aqueous methanol was adjusted to pH=6.25 with 1M NaOH. The mixture was concentrated and then redissolved in absolute methanol (20 ml). Methyl 2-oxo-4-phenylbutyrate (1.42 g) and 3A powdered molecular sieves (4 g) were added. A solution of sodium cyanoborohydride (277 mg) in 4 ml of methanol was added via a syringe pump over 24 hours. When reaction was complete, the sieves were removed by filtration and the filtrate concentrated. The residue was partitioned between CH$_2$Cl$_2$ and water. The CH$_2$Cl$_2$ layer was dried and concentrated to dryness. The mixture of diastereomers was separated by silica gel chromatography with 1:1 hexane:ethyl acetate as eluant.

The first diastereomer ($R_f=0.23$) eluted from the column was methyl [3R-[3α,6α(R*),9aβ]]-6from [(1-methoxycarbonyl-3-phenylpropyl)amino]octahydro-5oxothiazolo[3,2-a]azepine-3-carboxylate, 177 mg; $^1$H NMR (200MHz, CDCl$_3$)$\delta$1.52–2.14 (m, 8H), 2.71 (t, J =8 Hz, 2H), 3.18 (m, 4H), 3.66 (s, 3 H), 3.73 (s, 3H), 4.85 (d, J=9 Hz, 1H), 5.27 (dd, J=7 Hz, J=3 Hz, 1H), 7.26 (m, 5H); exact mass measurement, obs. 420.1711, calc'd. 420.1718; $[\alpha]_D^{25°}= -42.9°$ (CHCl$_3$)

Anal. Calc'd. for C$_{21}$H$_{28}$N$_2$O$_5$S: C, 59.98; H, 6.71; N, 6.66; S, 7.63. Found: C, 59.98; H, 6.76; N, 6.49; S, 7.35.

The second diastereomer ($R_f=0.29$) eluted from the column was methyl [3R-[3α,6α (S*),9aβ]]-6-[(1-methoxycarbonyl-3-phenylpropyl)amino]octahydro-5oxothiazolo[3,2-a]azepine-3-carboxylate, 290 mg; $^1$H NMR (200MHz, CDCl$_3$)$\delta$1.62–2.24 (m, 8H), 2.74 (t, J=8 Hz, 2H), 3.14–3.46 (m, 4H), 3.73 (s, 3H), 3.80 (s, 3H), 4.99 (d, J=9 Hz, 1H), 5.28 (dd, J=7 Hz, J =3 Hz, 1H), 7.28 (m, 5H); exact mass measurement, obs. 420.1711, calc'd. 420.1718; I.R. 1730 and 1650 cm$^{-1}$; $[\alpha]_D^{25°}= -65.8°$ (CHC13)

Anal. Calc'd. for C$_{21}$H$_{28}$N$_2$O$_5$S: C, 59.98; H, 6.71; N, 6.66; S, 7.63. Found: C, 60.24; H, 6.80; N, 6.47; S, 7.57.

This second diastereomer (195 mg) was dissolved in ethyl acetate (15 ml) and hydrogen chloride gas was passed through the solution. The ethyl acetate was removed at reduced pressure and the residue titurated with ether; $[\alpha]_D^{25°}= -55.6°$ (CH$_3$OH)

Anal. Calc'd. for C$_{21}$H$_{28}$N$_2$SO$_5$, Hcl: C, 55.19; H, 6.40; N, 6.13. Found: C, 55.20; H, 6.36; N, 5.49.

EXAMPLE 13

Methyl [3R-[3α,6α(S*),9aβ]]-6-[(1-methoxycarbonyl3-phenyl-propyl)amino]octahydro-1-oxo-5-oxothiazolo[3,2-]azepine-3-carboxylate To a solution of methyl [3R-[3α,6α(S*),9aβ]]6-[(1-methoxycarbonyl-3-phenylpropyl)amino]octahydro5-oxothiazolo[3,2-a]azepine-3-carboxylate hydrochloride (166.4 mg, 0.364 mmole) in 5 ml of chloroform at 0°, purified meta-chloroperoxybenzoic acid (MCPBA, 63 mg, 0.364 mmole) in 3 ml of chloroform was added. The reaction mixture was stirred at 0° for two hours prior to dilution with 50 ml of CH$_2$Cl$_2$. This solution was washed with a basic (pH 10) solution (2X), water (1X) and then dried with Na$_2$SO$_4$. The $^1$H NMR spectrum of the concentrate indicated a 60:40 mixture of isomeric sulfoxides. The diastereomeric sulfoxides were separated by column chromatography on silica gel (95:5 ethyl acetate:acetonitrile).

The first sulfoxide eluted from the column was assigned the (R) stereochemistry at the sulfoxide center based on the observed aromatic solvent induced shifts noted in the $^1$H NMR spectra (for a leading reference see: W. A. Nachtergaele and M. J. O. Anteunis, *Bull. Soc. Chim. Belg.*, 89, 749 (1980)); 74.3 mg. 200 MHz $^1$H NMR (CDCl$_3$):$\delta$1.40–2.28 (m, 8H), 2.50 (br s, 1H, NH), 2.72 (t, J=8 Hz, 2H), 2.89 (½ABq, J$_{AB}$=14 Hz, J$_{AX}$=10.5 Hz, 1H), 3.48 (m, 3H), 3.70 (s, 3H), 3.83 (s, 3H), 4.85 (d, J=12 Hz, 1H), 5.24 (dd, J$_{AX}$=10.5 Hz, J$_{BX}$=7 Hz, 1H), 7.24 (m, 5H). Mass spectrum shows peaks at 436, 419 and 377 m/e.

The second component eluted from the column is assigned the (S) stereochemistry at the sulfoxide center, 58 mg. 200 MHz $^1$H NMR (CDCl$_3$): δ 1.60–2.32 (m, 8H), 2.74 (t, J=8.5 Hz, 2H), 3.11 (½ ABq, J$_{AB}$=14.5 Hz, J$_{AX}$=8 Hz, 1H), 3.40 (m, 2H), 3.66 (½ ABq, J$_{AB}$=14.5 Hz, J$_{BX}$=2.5 Hz, 1H), 3.70 (s, 3H), 3.78 (s, 3H), 4.74 (d, J=9 Hz, 1H), 5.52 (dd, J$_{AX}$=8 Hz, J$_{BX}$=2.5 Hz, 1H), 7.26 (m, 5H). Mass spectrum shows peaks at 436, 419, 377 and 258 m/e.

EXAMPLE 14

Ethyl [3R-[3α,6α(S*),9aβ]]-6-[(1-Ethoxycarbonyl-3-phenyl-propyl)amino]octahydro-5-oxothiazolo[3,2-a]azepine-3-carboxylate hydrochloride Anhydrous hydrogen chloride was bubbled through a solution of [3R-[3α,6α(S*),9aβ]]-6-[(1-ethoxycarbonyl-3-phenylpropyl)amino]octahydro-5-oxo-thiazolo[3,2-a]azepine-3-carboxylic acid hydrochloride (116 mg) (Example 18) in absolute ethanol (30 ml) at 0° for 10 minutes. The reaction mixture was stirred overnight at room temperature and then taken to dryness under reduced pressure. The residue was partitioned between H$_2$O (10 ml) and ether (20 ml). To this mixture, 0.28 ml of 1M NaOH solution was added. After a few minutes, the layers were separated. The ethereal layer was dried (Na$_2$O$_4$) and then concentrated to give 100 mg of product. Chromatography on silica gel (2:1 Hexane:ethyl acetate, $R_f=0.26$) afforded 80 mg of pure product. The mass spectrum showed a molecular ion at 448. 'H NMR (200 MHz, CDCl₃) δ 1.32 (2 triplets, 6H), 1.60 (br s, 1H), 1.68–2.20 (m, 8H), 2.75 (t, J=8 Hz, 2H), 3.28 (m, 2H), 3.4 (m, 2H), 4.25 (m, 4H), 5.01 (d, J=10 Hz, 1H), 5.29 (dd, J=6 Hz, J=3 Hz, 1H), 7.28 (m, 5H). Anhydrous hydrogen chloride was bubbled through a solution of the purified diester in ether (30 ml) at 0°. Excess HCl was removed and the title product was collected by filtration, wt. 84 mg; m.p. 68°–70°; [α]$_D^{25°}$ = −52.98° (EtOH, c=0.44).

Anal. Calc'd. for C₂₃H₃₂N₂O₅S·HCl·½H₂O: C, 56.43; H, 6.90; N, 5.72. Found: C, 56.47; H, 6.95; N, 5.42.

EXAMPLE 15

Ethyl [3R-[3α,6α(S*),9aβ]]-6-[(1-Ethoxycarbonyl-3-phenylpropyl)amino]octahydro-1-oxo-5-oxothiazolo[3,2-a]azepine-3-carboxylate To a solution of ethyl [3R-[3α,6α(S*),9aβ]]-6-[(1-ethoxycarbonyl-3-phenylpropyl)amino]octahydro-5-oxotniazolo[3,2-a]-azepine-3-carboxylate hydrochloride (105 mg, 0.217 mmole) in 3 ml of chloroform at 0°, purified meta-chloroperoxybenzoic acid (37.5 mg, 0.217 mmole) in 3 ml of chloroform was added. The mixture was stirred at 0° for 3 hours. The reaction mixture was diluted with 50 ml of CH₂Cl₂ and washed with a basic (pH ~ 10) solution of sodium carbonate. After a water wash and drying with Na₂SO₄, concentration afforded a diastereomeric mixture of sulfoxides, wt. 98 mg. Mass spectrum showed a molecular ion at 464. NMR indicated a 2:1 mixture of the diastereomeric sulfoxides with the (R) sulfoxide as the major element. 200 MHz 'H NMR (in part, CDCl₃), 4.75 (d, J=10 Hz, 1H, minor diastereomer), 4.84 (d, J=12 Hz, 1H, major), 5.21 (dd, J=11 Hz, J=7 Hz, 1H, major), 5.49 (d, J=9 Hz, 1H, minor). Tlc [silica 9:1 ethyl acetate:acetonitrile] showed an unresolved single spot, R$_f$=0.44.

Anal. Calc'd. for C₂₃H₃₂N₂O₆S·HCl·0.5H₂O: C, 54.16; H, 6.72; N, 5.49; S, 6.29. Found: C, 54.20; H, 6.96; N, 5.91; S, 6.52.

EXAMPLE 16

Methyl [3R-[3α,6α(S*),9aα]]-6-[[1-(methoxycarbonyl)-3-phenylpropyl]amino]octahydro-5-oxothiazolo[3,2-a]azepine-3-carboxylate hydrochloride A solution of methyl [3R-(3α,6α,9aα)]-6-aminooctahydro-5-oxothiazolo[3,2-a]azepine-3-carboxylate hydrochloride (152 mg) in aqueous methanol (10 ml, 1:1) was adjusted to pH 6.2 with 0.5M NaOH solution. The solution was concentrated and then redissolved in absolute methanol (10 ml). Methyl 2-oxo-4-phenylbutyrate (0.78 g) and powdered 3A molecular sieves (1.5 g) were added. A solution of sodium cyanoborohydride (102 mg) in methanol (3.5 ml) was slowly added via a syringe pump. When the reaction was completed, the sieves were removed by filtration and the filtrate concentrated. The residue was partitioned between CH₂Cl₂ (50 ml) and water (50 ml). The CH₂Cl₂ layer was dried and then concentrated to dryness. The diastereomers were separated by silica gel chromatography with 1:1 hexane:ethyl acetate as eluant.

The first diastereomer (R$_f$=0.35) eluted from the column was methyl [3R-[3α,6α(R*), 9aα]]-6-[[1-(methoxycarbonyl)-3-phenylpropyl]amino]octahydro-5-oxothiazolo[3,2-a]azepine-3-carboxylate, wt. 78 mg. 'H NMR (200 MHz, CDCl₃) δ 1.53–2.22 (m, 8H), 2.72 (t, J=8 Hz, 2H), 3.12 (m, 1H), 3.28 (m, 1H), 3.54 (m, 1H), 3.66 (m, 1H), 3.76 (s, 6H), 5.24 (dd, J=7 Hz, J=3 Hz, 1H), 5.70 (d, J=10 Hz, 1H), 7.28 (m, 5H); exact mass measurement, obs. 420.1685, calc'd. 420.1718.

Anal Calc'd. for C₂₁H₂₈N₂O₅S: C, 59.98; H, 6.71; N, 6.66; S, 7.63. Found: C, 60.05; H, 6.93; N, 6.52; S, 7.79.

The second diastereomer (R$_f$=0.26) to come off the column was methyl [3R-[3α,6α(S*), 9aα]]-6-[[1-(methoxycarbonyl)-3-phenylpropyl]amino]octahydro-5-oxothiazolo[3,2-a]azepine-3-carboxylate wt. 120 mg. This isomer was recrystallized from ether-petroleum ether (1:1), m.p. 123.5°–24°. 'H NMR (200 MHz, CDCl₃) δ 1.60–2.23 (m, 8H), 2.84 (m, 2H), 3.14 (m, 1H), 3.30 (m, 1H), 3.63 (m, 2H), 3.74 (s, 3H), 3.76 (s, 3H), 5.24 (dd, J=7 Hz, J=3 Hz, 1H), 5.97 (d, J=10 Hz, 1H), 7.28 (m, 5H); exact mass measurement, obs. 420.1725, calc'd. 420.1718.

Anal. Calc'd. for C₂₁H₂₈N₂O₅S: C, 59.98; H, 6.71; N, 6.66; S, 7.63. Found: C, 60.12; H, 6.77; N, 6.46; S, 7.93.

This second diastereomer was dissolved in ethyl acetate and hydrogen chloride gas passed through the solution. Concentration under reduced pressure and trituration with ether afforded the hydrochloride salt as a solid.

EXAMPLE 17

Methyl [3R-[3α,6α(S*),9aα]]-6-[[1-(methoxycarbonyl)-3-phenylpropyl]amino]octahydro-1-oxo-5-oxothiazolo[3,2-a]azepine-3-carboxylate To a solution of methyl [3R-[3α,6α(S*),9aα]]-6-[[1-(methoxycarbonyl)-3-phenylpropyl]amino]octahydro-5-oxothiazolo[3,2-a]-azepine-3-carboxylate hydrochloride (18.3 mg, 0.04 mmole) in 2 ml of chloroform at 0°, purified meta-chloroperoxybenzoic acid (6.9 mg, 0.04 mmole) was added. The reaction mixture was stirred for 2.5 hours prior to work-up. Work-up consisted of dilution of the reaction mixture with 30 ml of chloroform, washing with a basic (pH=10) solution of sodium carbonate (2×), washing with water, and drying over Na₂SO₄. Concentration afforded an oil, 17 mg. 'H NMR examination indicated a 55:45 mixture of diastereomeric sulfoxides. 200 MHz 'H NMR (in part) (CDCl₃) 5.16 (dd, J=10 Hz, J=6 Hz, 1H, major diastereomer), 5.50 (d, J=11 Hz, 1H, major), 5.63 (d, J=8 Hz, 1H, minor), 5.90 (d, J=12 Hz, 1H, minor). Mass spectrum exhibited a molecular ion at 436. Tlc [silica, 9:1 ethyl acetate: acetonitrile] indicated two spots, R$_f$=0.46 and 0.40.

EXAMPLE 18

[3R-[3α,6α(S*),9aβ]]-6-[(1-Ethoxycarbonyl-3-phenylpropyl)amino]octahydro-5-oxothiazolo[3,2-a]azepine-3-carboxylic acid hydrochloride A solution of [3R-(3α,6α,9aβ)]-6-aminooctahydro-5-oxothiazolo[3,2-a]azepine-3-carboxylic acid (345 mg) in 10 ml of H₂O was adjusted to pH 6.3 with dilute NaOH. The solution was then freeze-dried. The residue and ethyl 2-oxo-4-phenylbutyrate (1.55 g) were partly dissolved in 25 ml of absolute ethanol. Powdered 3A molecular sieves (3.5 g) were added. To this mixture, a solution of sodium cyanoborohydride (282 mg) in 5 ml of ethanol was slowly added via a syringe pump. After completion of the reaction, the mixture was filtered and the filtrate taken to dryness. The residue was partitioned between water (100 ml) and ether (50 ml). The layers were separated. The aqueous layer was absorbed on strong acid ion-exchange resin and eluted with water, then 3% pyridine in water to yield the title product as a mixture of diastereomers, wt. 638 mg. Tlc on silica [1:1:1:1 ethyl acetate:n-butanol:water:acetic acid] indicated a major spot at $R_f=0.80$. Diastereomers were separated by chromatography on Sephadex LH-20 (MeOH, 2.54 cm×2 m).

The first diastereomer to elute from the column was [3R-[3α,6α(S*),9aβ]]-6-[(1-ethoxycarbonyl-3-phenylpropyl)amino]octahydro-5-oxothiazolo [3,2-a]azepine-3-carboxylic acid, wt. 338 mg; exact mass measurement, obs. 420.1715, calc'd. 420.1718; 'H NMR (200 MHz, CDCl$_3$) δ 1.29 (t, J=6 Hz, 3H), 1.56–2.22 (m, 8H), 2.74 (t, J=8 Hz, 2H), 3.18 (m, 1H), 3.42 (m, 3H), 3.77 (br s, 2H, exchangeable), 4.20 (m, 2H), 4.96 (d, J=8 Hz, 1H), 5.19 (br s, 1H), 7.25 (m, 5H). $^{13}$C NMR spectrum in CDCl$_3$/MeOH (3:1) showed single absorptions at 174.5, 172.8, 141.4, 128.7, 126.3, 64.1, 62.9, 61.4, 60.4, 60.3, 35.7, 34.9, 32.2, 31.9, 31.5, 28.3, and 14.4 ppm.

The second diastereomer to elute from the column was [3R-[3α,6α(R*),9aβ]]-6-[(1-ethoxycarbonyl-3-phenylpropyl)amino]octahydro-5-oxothiazolo[3,2-a]azepine-3-carboxylic acid, wt. 101 mg; exact mass measurement, obs. 420.1727, calc'd. 420.1718; 'H NMR (200 MHz, CDCl$_3$) δ 1.28 (t, J=7 Hz, 3H), 1.54–2.22 (m, 8H), 2.77 (t, J=7 Hz, 2H), 3.15 (m, 1H), 3.34 (m, 3H), 3.54 (br s, 2H, exchangeable), 4.19 (q, J=7 Hz, 2H), 4.88 (d, J=7 Hz, 1H), 5.24 (d, J=5 Hz, 1H), 7.27 (m, 5H).

Anhydrous hydrogen chloride was bubbled into a solution of [3R-[3α,6α(S*),9aβ]]-6-[(1-ethoxycarbonyl-3-phenylpropyl)amino]octahydro-5-oxothiazolo[3,2-a]azepine-3-carboxylic acid (320 mg) in ethyl acetate (30 ml) at 0°. Precipitate was collected, wt. 305 mg; m.p. 224°–25° (dec); $[α]_D^{25}=-38.5°$ (EtOH, c=1.2); I.R. (KBr):1730, 1690, and 1658 cm$^{-1}$; Tlc on silica [1:1:1:1 ethyl acetate: n-butanol:water:acetic acid] indicated a single spot at $R_f=0.81$.

Anal. Calc'd. for $C_{21}H_{28}N_2O_5S.HCl.\frac{1}{2}H_2O$: C, 54.12; H, 6.49; N, 6.01; S, 6.88; Cl, 7.61. Found: C, 54.19; H, 6.47; N, 6.07; S, 6.71; Cl, 7.85.

EXAMPLE 19

[3R-[3α,6α(S*),9aβ]]-6-[(1-Ethoxycarbonyl-3-phenylpropyl)amino]octahydro-1-oxo-5-oxothiazolo[3,2-a]azepine-3-carboxylic acid To a solution of [3R-[3α,6α(S*),9aβ]]-6[(1-Ethoxycarbonyl-3-phenylpropyl)amino]octahydro-5oxothiazolo[3,2-a]azepine-3-carboxylic acid hydrochloride (252 mg, 0.55 mmole) in 50 ml of absolute ethanol at 0° under nitrogen, purified meta-chloroperoxybenzoic acid (100 mg, 0.58 mmole) was added. The reaction mixture was stirred for 2 hours and then added to an ion-exchange column (Dowex 50 X-2, 50-100 mesh, 15 ml). The column was eluted with an ethanol-water mixture (1:1) and then with water. The product was recovered with 4% pyridine-water elution. The appropriate fraction was freeze-dried to afford a white material, wt. 237 mg. HPLC analysis on a RP-18 column (Hibar-II, LiChrosorb RP-18, 10 μm) indicated a mixture of sulfoxides in a ratio of 98:2. 'H NMR examination permitted the assignment of the sulfoxide stereocenter in the major product as (R). Tlc of the mixture on silica gel [1:1:1:1 ethyl acetate:n-butanol:water:acetic acid] indicated a single spot, $R_f=0.54$. Mass spectrum showed a weak molecular ion at 436. 200 MHz 'H NMR (DMSO) δ 1.21 (t, J=7.5 Hz, 3H), 1.30–2.04 (m, 8H), 2.63 (t, J=8 Hz, 2H), 3.05 ($\frac{1}{2}$ ABq, $J_{AB}=14$ Hz, $J_{AX}=11$ Hz, 1H), 3.33 (t, J=6.5 Hz, 1H), 3.56 ($\frac{1}{2}$ABq, $J_{AB}=14$ Hz, $J_{BX}=6.5$ Hz, 1H), 3.65 (d, J=9 Hz, 1H), 4.10 (q, J=7.5 Hz, 2H), 4.80 (dd, $J_{AX}=11$ Hz, $J_{BX}=6.5$ Hz, 1H), 5.13 (d, J=11 Hz, 1H), 7.27 (m, 5H).

Anal. Calc'd. for $C_{21}H_{28}N_2O_6S.\frac{1}{2}H_2O$: C, 56.60; H, 6.56; N, 6.29; S, 7.20. Found: C, 56.46; H, 6.23; N, 6.17; S, 7.02.

EXAMPLE 20

[3R-[3α,6α(S*),9aβ]]-6-[(1-Carboxy-3-phenylpropyl)amino]octahydro-1-oxo-5-oxothiazolo[3,2-a]azepine-3carboxylic acid To a solution of [3R-[3α,6α(S*),9aβ]]-6-[(1-ethoxycarbonyl-3-phenylpropyl)amino]octahydro-1-oxo-5-oxothiazolo[3,2-a]azepine-3-carboxylic acid (Example 19) (130 mg, 0.3 mmole) in 4 ml of a methanol-water 1:1 mixture, 0.9 ml of 1N NaOH was added. The reaction mixture was stirred at room temperature overnight. The mixture was absorbed onto an ion-exchange resin (Dowex 50 X-2, 50-100 mesh, acid cycle, 15 ml) and eluted with water. The product was recovered with 4% pyridine in water. The appropriate fraction was freeze-dried to give a white material, wt. 114 mg. Tlc indicated a single spot, $R_f=0.49$ [silica, 1:1:1:1 ethyl acetate:n-butanol:water:acetic acid]. HPLC analysis on a reverse phase column (Hibar-II, LiChrosorb RP-18, 10 μm) indicated a 98.2 ratio of diastereomeric sulfoxides (R:S) 200 MHz 'H NMR (DMSO) δ 1.23–2.12 (m, 8H), 2.68 (m, 2H), 3.09 ($\frac{1}{2}$ABq, $J_{AB}=14$ Hz, $J_{AX}=11$ Hz, 1H), 3.29 (t, J=6 Hz, 1H), 3.62 ($\frac{1}{2}$ABq, $J_{AB}=14$ Hz, $J_{BX}=6.5$ Hz, 1H), 3.88 (d, J=11 Hz, 1H), 4.84 (dd, $J_{AX}=11$ Hz, $J_{BX}=6.5$ Hz, 1H), 5.18 (d, J=12 Hz, 1H), 7.28 (m, 5H).

Anal. Calc'd. for $C_{19}H_{24}N_2O_6S.1.5H_2O$: C, 52.40; H, 6.25; N, 6.43; S, 7.36. Found: C, 52.23; H, 5.89; N, 6.40; S, 7.56.

EXAMPLE 21

[3R-[3α,6α(S*R*),9aα]]-6-[[1-(Ethoxycarbonyl)-3-phenylpropyl]amino]octahydro-5-oxothiazolo[3,2-a]azepine-3-carboxylic acid hydrochloride A solution of [3R-(3α,6α,9aα)]-6-aminooctahydro-5-oxothiazolo[3,2-a]azepine-3-carboxylic acid (0.133 g) in 10 ml of water was adjusted to pH 6.7 with dilute NaOH solution. The solution was then freeze-dried. The residue and ethyl 2-oxo-4-phenylbutyrate (0.596 g) were dissolved in 10 ml of absolute ethanol. Powdered 3A molecular sieves (1.5 g) were added. To this mixture, a solution of sodium cyanoborohydride (0.109 g) in 2 ml of ethanol was slowly added via a syringe pump. When the reaction was completed, the mixture was filtered and the filtrate concentrated. The residue was partitioned between water (50 ml) and ether (50 ml). The layers were separated and the aqueous phase was absorbed on strong acid ion-exchange resin. Elution with water and then 3% pyridine in water permitted the isolation of the title compound as a mixture of diastereomers, wt. 200 mg. The mass spectrum was consistent with the structure and HPLC analysis (reverse phase) indicated approximately a 60:40 mixture of diastereomers. 'HNMR (200 MHz, CDCl$_3$) δ 1.25 (t, J=7 Hz, 3H), 1.52–2.20 (m, 8H), 2.74 (m, 2H), 3.23 (m, 2H), 3.54 (m, 2H), 4.18 (m, 2H), 5.22 (m, 1H), 5.64 and 5.92 (d, 1H) 5.82 (br s, 2H, exchangeable), 7.26 (m, 5H). The product was dissolved in ethyl acetate and anhydrous hydrogen chloride gas was passed through the solution. Concentration under reduced pressure and tituration with ethyl acetate gave the hydrochloride mixture as a solid.

EXAMPLE 22

[3R-[3α,6α(S*R*),9aα]]-6-[[1-(Ethoxycarbonyl)-3-phenylpropyl]amino]octahydro-1-oxo-5-oxo-thiazolo[3,2-a]azepine-3-carboxylic acid To a solution of [3R-[3α,6α(S*R*),9aα]]-6-[[1-(ethoxycarbonyl)-3-phenylpropyl]amino]octahydro-5-oxothiazolo[3,2-a]azepine-3-carboxylic acid hydrochloride (1 mmole) in 50 ml of absolute ethanol at 0° under nitrogen, purified meta-chloroperoxybenzoic acid (1.05 mmole) can be added. The reaction mixture can be stirred for 3 hours at 0° and then absorbed onto a Dowex 50 X-2 ion-exchange column. Elution with ethanol-water (1:1) and then 4% pyridine-water will permit recovery of the product. The product can then be freeze-dried to afford a mixture of diastereomeric sulfoxides which can be separated by preparative chromatography on a reverse-phase column.

EXAMPLE 23

[3R-[3α,6α(S*R*),9aα]]-6-[[1-Carboxy-3-phenylpropyl]amino]octahydro-1-oxo-5-oxothiazolo[3,2-a]azepine-3-carboxylic acid To a solution of [3R-[3α,6α(S*R*),9aα]]-6-[[1-(ethoxycarbonyl)-3-phenylpropyl]amino]octahydro-1-oxo-5-oxothiazolo[3,2-a]azepine-3-carboxylic acid (0.5 mmole) in 4 ml of a methanol-water mixture (1:1), 1.5 ml of 1N NaOH can be added. The reaction mixture can be stirred overnight at room temperature and then absorbed onto a strong acid ion-exchange resin such as Dowex 50 X-2, 50–100 mesh. The column can then be first eluted with water and then with 4% pyridine-water. The appropriate fraction can be freeze-dried to give the product as a diastereomeric mixture which can be separated by reverse-phase chromatography.

EXAMPLE 24

[3R-[3α,6α(S*),9aβ]]-6-[[1-(Ethoxycarbonyl)-3-(4-fluoro-phenyl)propyl]amino]octahydro-5-oxo-thiazolo[3,2-a]azepine-3-carboxylic acid hydrochloride A solution of [3R-[3α,6α,9aβ]]-6-aminooctahydro-5-oxothiazolo[3,2-a]azepine-3-carboxylic acid (0.23 g, 1.0 mmole) and ethyl 2-oxo-4-(4-fluorophenyl)butyrate (1.68 g, 7.5 mmole) in 16 ml of absolute ethanol was partly dissolved in 16 ml of absolute ethanol. Powdered 3A molecular sieves (2.6 g) were added. To this mixture, a solution of sodium cyanoborohydride (0.189 g, 3.0 mmole) in 2 ml of absolute ethanol was slowly added via a syringe pump. After completion of the reaction (17 hours), the mixture was filtered and the filtrate concentrated under reduced pressure. The residue was partitioned between water (40 ml) and ether (20 ml). The layers were separated and the aqueous layer was absorbed on strong acid ion-exchange resin (Dowex 50 X-2) (50 ml). The column was washed with MeOH/H$_2$O (1/1), water, and then 3.5% pyridine/water. Appropriate fractions were freeze-dried to afford 0.309 g of product as a mixture of diastereomers. Tlc on silica [1:1:1:1 ethyl acetate:n-butanol:water: acetic acid] indicated a single spot, R$_f$=0.72. Diastereomers were separated by chromatography on Sephadex LH-20 (MeOH, 2.54 cm×2 m).

The first diastereomer to elute from the column was the desired [3R-[3α,6α(S*),9aβ]]-6-[(1-(ethoxycarbonyl)-3-(4-fluorophenyl)propyl)amino]octahydro-5-oxothiazolo[3,2-a]azepine-3-carboxylic acid, 171 mg. 200 MHz 'H NMR (CDCl$_3$) δ 1.28 (t, J=7 Hz, 3H), 1.6–2.16 (m, 8H), 2.72 (t, J=8 Hz, 2H), 3.0 (br s, 2H, active hydrogens), 3.16 (½ABq, J$_{AB}$=13 Hz, J$_{AX}$=7 Hz, 1H), 3.40 (m, 3H), 4.20 (m, 2H), 4.96 (m, 1H), 5.20 (dd, J=7 Hz, J=1.5 Hz, 1H), 6.97 (t, 2H), 7.16 (m, 2H). The hydrochloride salt was prepared in ethyl acetate with gaseous hydrogen chloride.

Anal. Calc'd. for C$_{21}$H$_{27}$FN$_2$O$_5$S- HCl-1.25H$_2$O: C, 50.70; H, 6.18; N, 5.63. Found: C, 50.85; H, 6.06; N, 5.59.

The second diastereomer to elute from the column was [3R-[3α,6α(R*),9aβ]]-6-[(1-(ethoxycarbonyl)-3-(4-fluorophenyl)propyl)amino]octahydro-5-oxothiazolo[3,2-a]azepine-3-carboxylic acid, 86 mg.

EXAMPLE 25

[3R-[3α,6α(S*),9aβ]]-6-[[1-Ethoxycarbonyl)-3-(4-fluorophenyl)propyl]amino]octahydro-1-oxo-5-oxo-thiazolo[3,2-a]azepine-3-carboxylic acid A solution of [3R-[3α,6α,(S*),9aβ]]-6-[[1-(ethoxycarbonyl)-3-(4-fluorophenyl)propyl]amino]octahydro-5-oxothiazolo[3,2-a]azepine-3-carboxylic acid hydrochloride (54 mg, 0.114 mmole) and purified meta-chloroperoxybenzoic acid (20.7 mg, 0.120 mmole) in 5 ml of absolute ethanol was stirred for 2 hours. The reaction mixture was diluted with 5 ml of water and then absorbed onto a strong acid ion-exchange resin (Dowex 50 X-2, 50–100 mesh, 8 ml). Elution first with water and then with 4% pyridine-water afforded, after freeze-drying, 46.3 mg of a white material. 'H NMR studies permitted the assignment of stereochemistry at the sulfoxide center as (R). Tlc [silica, 1:1:1:1 ethyl acetate:n-butanol:water:acetic acid] indicated a single spot at R$_f$=0.61. Mass spectrum showed a molecular ion at 454 and a major peak at 381 m/e. 200 MHz 'H NMR (DMSO) δ 1.17 (t, J=7 Hz, 3H), 1.20–2.04 (m, 8H), 2.58 (t, J=7 Hz, 2H), 3.00 (½ ABq, J$_{AB}$=15 Hz, J$_{AX}$=12 Hz, 1H), 3.27 (m, 1H, and active hydrogens), 3.54 (m, 2H), 4.04 (q, J=7 Hz, 2H), 4.74 (dd, J$_{AX}$=12 Hz, J$_{BX}$=6 Hz, 1H), 5.09 (d, J=11 Hz, 1H), 7.00–7.28 (m, 4H).

EXAMPLE 26

[3R-[3α,6α(S*),9aβ]]-6-[[1-Carboxy-3-(4-fluorophenyl)-propyl]amino]octahydro-1-oxo-5-oxothiazolo[3,2-a]azepine-3-carboxylic acid To a solution of [3R-[3α,6α(S*),9aβ]]-6-[[1-(ethoxycarbonyl)-3-(4-fluorophenyl)propyl]amino]octahydro-1-oxo-5-oxothiazolo[3,2-a]azepine-3-carboxylic acid (14.5 mg, 0.33 mmole) in 0.75 ml of methanol, 0.75 ml of 1M NaOH solution was added. The reaction mixture was stirred for 1 hour before removing the methanol under reduced pressure. The resulting aqueous solution was stirred overnight at room temperature. The mixture was absorbed onto Dowex 50 X-2, 50–100 mesh (8 ml) ion-exchange resin. The column was eluted with water then 4% pyridine-water. The appropriate fraction was freeze-dried to give 13 mg of product. Tlc [silica, 1:1:1:1 ethyl acetate:n-butanol:water:acetic acid] showed a single spot, R$_f$=0.52. 200 MHz 'H NMR (DMSO) was consistent with the (R) stereochemistry at the sulfoxide: 1.20–2.12 (m, 8H), 2.67 (m, 2H), 3.10 (½ ABq, J$_{AB}$=15 Hz, J$_{AX}$=11 Hz, 1H), 3.38 (br s, 1H), 3.60 (½ ABq, J$_{AB}$=15 Hz, J$_{BX}$=7 Hz, 1H), 3.98 (d, J=10 Hz, 1H), 4.83 (dd, J$_{AX}$=11 Hz, J$_{BX}$=7 Hz, 1H), 5.19 (d, J=12 Hz, 1H), 7.14 (t, J=9 Hz, 2H), 7.29 (m, 2H).

EXAMPLE 27

[3R-[3α,6α(S*),9aβ]]-6-[(1-(Ethoxycarbonyl)-4-methylpentyl)amino]octahydro-5-oxothiazolo[3,2-a]azepine-3-carboxylic acid hydrochloride To a solution of [3R-(3α,6α,9aβ)]-6-aminooctahydro-5-oxothiazolo[3,2-a]azepine-3-carboxylic acid (0.348 g) and ethyl 5-methyl-2-oxo-hexanoate (1.30 g) in absolute ethanol (15 ml), powdered 3A molecular sieves (3.9 g) were added. To this mixture, a solution of sodium cyanoborohydride (0.285 g) in ethanol (2 ml) was slowly added. When the reaction was completed, the mixture was filtered and the filtrate concentrated to dryness. The residue was partitioned between water (35 ml) and ether (35 ml) and the layers were separated. The aqueous layer was acidified with 1M $H_3PO_4$ to pH 4.5 and then extracted repeatedly with chloroform. The chloroform layers were dried and then concentrated to yield product, wt. 0.538 g. Separation of the (S*,R*) diastereomers was achieved by chromatography on Sephadex LH-20 (MeOH).

The first diastereomer off the column was the (S*) isomer: wt. 0.219 g; exact mass measurement, obs. 386.1855, calc'd. 386.1874. Tlc on silica [1:1:1:1 ethyl acetate:n-butanol:water:acetic acid] indicated a single spot, $R_f$=0.83. 'H NMR (200 MHz, $CD_3OD$) δ 0.92 (dd, J=7 Hz, J=2.5 Hz, 6H), 1.30 (t, J=7 Hz, 3H), 1.32 (m, 2H), 1.57 (m, 1H), 1.70–2.26 (m, 8H), 3.24 (m, 2H), 3.68 (t, J=6.5 Hz, 1H), 3.86 (d, J=10 Hz, 1H), 4.26 (m, 2H), 5.08 (m, 2H).

The second diastereomer to elute from the column was the (R*) isomer: wt. 0.210 g; exact mass measurement, obs. 386.1847, calc'd. 386.1874. 'H NMR (200 MHz, $CD_3OD$) δ 0.91 (d, J=7 Hz, 6H), 1.20 (m, 2H), 1.28 (t, J=8 Hz, 3H), 1.54 (m, 1H), 1.64–2.20 (m, 8H), 3.23 (m, 2H), 3.49 (m, 2H), 4.21 (m, 2H), 5.13 (m, 2H).

Anhydrous hydrogen chloride was bubbled through a solution of [3R-[3α,6α(S*),9aβ]]-6-[(1-ethoxycarbonyl-4-methylpentyl)amino]octahydro-5-oxothiazolo[3,2-a]azepine-3-carboxylic acid (114 mg) in ethyl acetate (10 ml) at 0°. Upon removal of excess HCl, the precipitate was collected, wt. 0.120 g [α]$_D^{25}$=−54.7° (MeOH, c=0.5).

Anal. Calc'd. for $C_{18}H_{30}N_2O_5S$·HCl·0.5$H_2O$: C, 50.05; H, 7.47; N, 6.49; S, 7.42; Cl, 8.21. Found: C, 49.74; H, 7.36; N, 6.31; S, 7.39; Cl, 8.39.

EXAMPLE 28

[3R-[3α,6α(S*),9aβ]]-6-[(1-Ethoxycarbonyl-4-methylpentyl)amino]octahydro-1-oxo-5-oxothiazolo[3,2-a]azepine-3-carboxylic acid A solution of [3R-[3α,6α(S*),9aβ]]-6-[(1-ethoxycarbonyl-4-methylpentyl)amino]octahydro-5-oxothiazolo[3,2-a]azepine-3-carboxylic acid hydrochloride (50 mg, 0.118 mmole) and purified metachloroperoxybenzoic acid (21 mg, 0.124 mmole) in 5 ml of absolute ethanol was stirred at 0° for 2 hours. The reaction mixture was diluted with 5 ml of water and then absorbed onto 8 ml of Dowex 50 X-2, 50–100 mesh resin (acid cycle). The column was eluted with water followed by 4% pyridine-water. The appropriate fraction was freeze-dried to afford a white product, wt. 38.3 mg. Tlc on silica [1:1:1:1 ethyl acetate: n-butanol:water:acetic acid] indicated a single spot, $R_f$=0.60. Sulfoxide stereochemistry was assigned as (R). Mass spectrum showed a weak molecular ion at 402 and 385. Base peak appeared at 329 m/e. 200 MHz 'H NMR (DMSO) δ 0.88 (d, J=7 Hz, 6H), 1.24 (t, J=6 Hz, 3H), 1.27–2.04 (m, 11H), 3.09 (½ ABq, $J_{AB}$=14 Hz, $J_{AX}$=12 Hz, 1H), 3.28 (m, 1H), 3.64 (m, 2H), 4.14 (m, 2H), 4.82 (dd, $J_{AX}$=12 Hz, $J_{BX}$=6 Hz, 1H), 5.15 (d, J=12 Hz, 1H).

EXAMPLE 29

[3R-[3α,6α(S*),9aβ]]-6-[(1-Carboxy-4-methylpentyl)amino]octahydro-1-oxo-5-oxothiazolo[3,2-a]azepine-3-carboxylic acid Sodium hydroxide solution (0.75 ml, 1M) was added to a methanolic (0.75 ml) solution of [3R-[3α,6α(S*),9aβ]]-6-[(1-ethoxycarbonyl-4-methylpentyl)amino]octahydro-1-oxo-5-oxothiazolo[3,2-a]azepine-3-carboxylic acid (16.6 mg, 0.043 mmole). After 1 hour, the methanol was removed under reduced pressure and the resulting aqueous solution was stirred overnight at room temperature. The reaction mixture was absorbed onto Dowex 50 X-2, 50–100 mesh (8 ml) and eluted with water then 4% pyridine-water. The appropriate fraction was freeze-dried to give 15 mg of pure product. Tlc [silica, 1:1:1:1 ethyl acetate: n-butanol:water:acetic acid] indicated a single spot, $R_f$=0.49. 200 MHz 'H NMR (DMSO) δ 0.86 (d, J=7 Hz, 6H), 1.10–2.10 (m, 11H), 3.09 (½ABq, $J_{AB}$=4.5 Hz, $J_{AX}$=11 Hz, 1H), 3.22 (t, J=6 Hz, 1H), 3.59 (½ABq, $J_{AB}$=14.5 Hz, $J_{BX}$=6 Hz, 1H), 4.83 (d, J=10.5 Hz, 1H), 4.82 (dd, $J_{AX}$=11 Hz, $J_{BX}$=6 Hz, 1H), 5.16 (d, J=11 Hz, 1H).

EXAMPLE 30

Benzyl [3R-[3α,6α(S*),9aβ]]-6-[(1-Benzyloxycarbonyl-3phenylpropyl)amino]octahydro-5-oxothiazolo[3,2-a]azepine-3-carboxylate hydrochloride To a solution of benzyl [3R-[3α,6α,9aβ]]-6-aminooctahydro-5-oxothiazolo[3,2-a]azepine-3-carboxylate (0.5 mmole) and benzyl 2-oxo-4-phenylbutyrate (2.5 mmole) in absolute ethanol (12 ml), powdered 3A molecular sieves (2.5 g) and 0.029 ml of acetic acid can be added. To this mixture, a solution of sodium cyanoborohydride (1.5 mmole) in 2.5 ml of absolute ethanol can be added slowly via a syringe pump. When the reaction is completed (fluorescamine assay), the mixture can be filtered and the filtrate concentrated. The residue can be partitioned between water and $CH_2Cl_2$. The organic layer can be dried and concentrated to afford the crude product. Chromatography on silica gel will permit the isolation of the two expected diastereomers. Structural assignment can be made based on the conversion of one of the diastereomers into [3R-[3α,6α(S*),9aβ]]-6-[(1-carboxy-3-phenylpropyl)amino]octahydro-5-oxothiazolo[3,2-a]-azepine-3-carboxylic acid by catalytic hydrogenolysis (10% Pd/C) or alkaline hydrolysis. The (S*) diastereomer can be dissolved in ethyl acetate and anhydrous hydrogen chloride gas can be passed through the solution. Concentration and tituration with ether will produce the hydrochloride salt.

EXAMPLE 31

Benzyl [3R-[3α,6α(S*),9aβ]]-6-[(1-Benzyloxycarbonyl-3-phenylpropyl)amino]octahydro-1-oxo-5-oxothiazolo[3,2-a]azepine-3-carboxylate To a solution of benzyl [3R-[3α,6α(S*),9aβ]]-6-[(1-benzyloxycarbonyl-3-phenylpropyl)amino]octahydro-5-oxothiazolo[3,2-a]azepine-3-carboxylate hydrochloride (0.5 mmole) in 7 ml of chloroform at 0°, purified meta-chloroperoxybenzoic acid (0.5 mmole) in 3 ml of chloroform can be added. The reaction mixture can then be stirred at 0° for 3 hours. The organic solution can be washed with a basic (pH 10) solution (2×) and then water. The solution can be dried (Na₂SO₄) and then concentrated to afford the product as a mixture of diastereomeric sulfoxides. The diastereomers can be separated by column chromatography. The stereochemical assignment can be made on the basis of NMR studies as in Example 13.

EXAMPLE 32

[3R-[3α,6α(S*),9aβ]]-6-[(1-Carboxy-3-phenylpropyl)amino]octahydro-1(R)-oxo-5-oxothiazolo[3,2-a]azepine-3-carboxylic acid A solution of benzyl [3R-[3α,6α(S*),9aβ]]-6-[(1-benzyloxycarbonyl-3-phenylpropyl)amino]octahydro-1(R)-oxo-5-oxothiazolo[3,2-a]azepine-3-carboxylate (0.2 mmole) in 30 ml of absolute ethanol, which contains 3 equivalents of acetic acid, can be hydrogenated at 1 atmosphere of hydrogen over 10% palladium on carbon. When the reaction is complete, the catalyst can be removed by filtration and the filtrate concentrated to give the 1(R)-sulfoxide.

EXAMPLE 33

[3R-[3α,6α(S*),9aβ]]-6-[(1-Carboxy-3-phenylpropyl)amino]octahydro-1(S)-oxo-5-oxothiazolo[3,2-a]azepine-3carboxylic acid A solution of benzyl [3R-[3α,6α(S*),9aβ]]-6-[(1-benzyloxycarbonyl-3-phenylpropyl)amino]octahydro-1(S)-oxo-5-oxothiazolo[3,2-a]azepine-3-carboxylate (0.1 mmole) and 3 equivalents of acetic acid in 15 ml of absolute ethanol can be hydrogenated at 1 atmosphere of hydrogen over 10% palladium on carbon. The reaction can be monitored by tlc. When the reaction is complete, the catalyst can be removed by filtration and the filtrate concentrated to give the 1(S)-sulfoxide.

EXAMPLE 34

Benzyl [3R-[3α,6α(S*),9aα]]-6-[(1-benzyloxycarbonyl-3-phenylpropyl)amino]octahydro-5-oxothiazolo[3,2-a]-azepine-3-carboxylate hydrochloride To a solution of benzyl [3R-[3α,6α(S*),9aα]]-6-aminooctahydro-5-oxothiazolo[3,2-a]azepine-3-carboxylate (1.0 mmole) and benzyl 2-oxo-4-phenylbutyrate (5.0 mmole) in absolute ethanol (25 ml), powdered 3A molecular sieves (5 g) and 0.058 ml of acetic acid can be added. To this mixture a solution of sodium cyanoborohydride (3.0 mmole) in 5 ml of ethanol can be added over 18 hours (syringe pump). The reaction can be followed with a fluorescamine assay. Upon completion of the reaction, the mixture can be filtered and the filtrate concentrated. The residue can be partitioned between water and CH₂Cl₂. The organic layer can be concentrated and the residue chromatographed on silica gel. The (R*) and (S*) diastereomers (at the new center) can be isolated. The absolute stereochemistry at the new center can be assigned based on its correlation with [3R-[3α,6α(S*),9aα]]-6-[(1-carboxy-3-phenylpropyl)amino]octahydro-5-oxothiazolo[3,2-a]azepine-3carboxylic acid (Example 40) via alkaline hydrolysis. The (S*) diastereomer can be dissolved in ethyl acetate and anhydrous hydrogen chloride gas can be passed through the solution. Concentration and tituration with ether will produce the hydrochloride salt.

EXAMPLE 35

Benzyl [3R-[3α,6α(S*),9aα]]-6-[(1-benzyloxycarbonyl-3-phenylpropyl)amino]octahydro-1-oxo-5-oxothiazolo[3,2-a]azepine-3-carboxylate To a solution of benzyl [3R-[3α,6α(S*),9aα]]-6-[(1-benzyloxycarbonyl-3-phenylpropyl)amino]octahydro-5-oxothiazolo[3,2-a]azepine-3-carboxylate hydrochloride (0.5 mmole) in 7 ml of chloroform at 0°, purified meta-chloroperoxybenzoic acid (0.5 mmole) in 3 ml of chloroform can be added. The reaction mixture can be stirred at 0° for 3 hours. The mixture can then be diluted with CH₂Cl₂ and the resulting solution washed with a basic (pH=10) solution (2×) and then water. The solution can be dried and concentrated to give a mixture of the diastereomeric sulfoxides. The diastereomers can be separated by column chromatography. Stereochemical assignments can be made by NMR studies (aromatic solvent induced shifts).

EXAMPLE 36

[3R-[3α,6α(S*),9aα]]-6-[(1-carboxy-3-phenylpropyl)amino]octahydro-1(R)-oxo-5-oxothiazolo[3,2-a]-azepine-3-carboxylic acid A solution of benzyl [3R-[3α,6α(S*),9aα]]-6-[(1-benzyloxycarbonyl-3-phenylpropyl)amino]octahydro-1(R)-oxo-5-oxothiazolo[3,2-a]azepine-3-carboxylate (0.3 mmole) and 3 equivalents of acetic acid in 40 ml of absolute ethanol can be hydrogenated at 1 atmosphere of hydrogen over 10% palladium on carbon. The reaction can be monitored (tlc, HPLC). When the reaction is complete, the catalyst can be removed by filtration. Concentration and drying of the filtrate will afford the 1(R)-sulfoxide.

EXAMPLE 37

[3R-[3α,6α(S*),9aα]]-6-[(1-carboxy-3-phenylpropyl)-[amino]octahydro-1 (S)-oxo-5-oxothiazolo[3,2-a]azepine-3-carboxylic acid A solution of benzyl [3R-[3α,6α(S*),9aα]]-6[(1-benzyloxycarbonyl-3-phenylpropyl)amino]octahydro-1(S)-oxo-5-oxothiazolo[3,2-a]azepine-3-carboxylate (0.15 mmole) and three equivalents of acetic acid in 40 ml of absolute ethanol can be hydrogenated over 10% palladium on carbon at 1 atmosphere of hydrogen. The reaction can be terminated upon completion and the catalyst removed by filtration. The filtrate can then be concentrated and dried to give the 1(S)-sulfoxide product.

EXAMPLE 38

[3R-[3α,6α(S*),9aβ]]-6-[(1-Carboxy-3-phenylpropyl)amino]octahydro-5-oxothiazolo[3,2-a]azepine-3carboxylic acid Methyl [3R-[3α,6α(S*),9aβ]]-6-[(1-methoxy- carbonyl-3-phenylpropyl)amino]octahydro-5-oxothiazolo[3,2-a]azepine-3-carboxylate (Example 12) (180 mg) was dissolved in 2 ml of CH₃OH and 2 ml of 1M NaOH. After standing overnight, the product was absorbed on strong acid ion-exchange resin and eluted with 3% pyridine in water. Appropriate fraction was concentrated and dried in vacuo to afford a white solid, 165 mg. Recrystallized from methanol, m.p. 212°-13° (dec); $[\alpha]_D^{25°} = -90.9°$ (0.1N NaOH, c=0.2); I.R. (KBr) 1718 and 1654 cm⁻¹; Tlc on silica 1:1:1:1 ethyl acetate:n-butanol:water:acetic acid]indicated a single product, R$_f$=0.78; $^1$H NMR (200 MHz, d$_6$-DMSO) δ 1.36–2.20 (m, 8H), 2.69 (m, 2H), 3.24 (m, 3H), 3.81 (d, J=10 Hz, 1H), 5.07 (dd, J=7 Hz, J=3.5 Hz, 1H) 5.19 (d, J=8 Hz, 1H), 7.26 (m, 5H). The mass spectrum showed a molecular ion at 536 m/e for the disilylated species. X-ray crystal structure analysis established the stereochemistry of the side chain as (S).

Anal. Calc'd. for C$_{19}$H$_{24}$N$_2$O$_5$S-½H$_2$O: C, 56.84; H, 6.28; N, 6.98; S, 7.99. Found: C, 56.68; H, 6.11; N, 6.82; S, 7.87.

EXAMPLE 39

[3R-[3α,6α(S*),9aβ]]-6-[(1-Carboxy-3-phenylpropyl)amino]octahydro-1,1-dioxo-5-oxothiazolo[3,2-a]azepine-3-carboxylic acid To a solution of [3R-[3α,6α(S*),9aβ]]-6-[(1-carboxy-3-phenylpropyl)amino]octahydro-5-oxothiazolo[3,2-a]azepine-3-carboxylic acid (18.8 mg, 0.05 mmole) in 0.6 ml of glacial acetic acid at 0°, a solution of KMnO$_4$ (10.6 mg, 0.067 mmole) in 0.6 ml of water was added via a syringe pump over 1.5 hours. The reaction mixture was then passed through a Dowex 50 X-2, 50–100 mesh (50 ml) ion-exchange column (acid cycle). The column was eluted with water then 4% pyridine-water. The appropriate fraction was freeze-dried to afford 0.011 g of product. The sulfone was purified by chromatography on a reverse-phase column. The product exhibited $^1$H NMR spectral characteristics consistent with its structure.

EXAMPLE 40

[3R-[3α,6α(S*),9aα]]-6-[(1-Carboxy-3-phenylpropyl)amino]octahydro-5-oxothiazolo[3,2-a]azepine-3-carboxylic acid Methyl [3R-[3α,6α(S*),9aα]]-6-[[1-(methoxycarbonyl)-3-phenylpropyl]amino]octahydro-5-oxothiazolo[3,2-a]azepine-3-carboxylate (Example 16) (125 mg) was dissolved in 1 ml of MeOH and 2 ml of 1M NaOH solution (gentle heating was required). After standing overnight at room temperature, the reaction mixture was absorbed on strong acid ion-exchange resin and eluted with 3% pyridine in water. The appropriate fraction was concentrated and dried to afford a white solid, wt. 99 mg. Recrystallized from water-methanol to give fine white needles, wt. 76 mg; m.p. 191.5°–93° (dec); Tlc on silica [1:1:1:1 ethyl acetate:n-butanol:water:acetic acid] indicated a single component, R$_f$=0.75; I.R. (KBr): 1725 and 1622 cm$^{-1}$; $^1$H NMR (200 MHz, d$_6$-DMSO) δ 1.42–2.24 (m, 8H), 2.76 (m, 2H), 3.03 (dd, J=12 Hz, J=2.5 Hz, 1H), 3.38 (m, 3H), 4.99 (d, J=5 Hz, 1H), 5.94 (d, J=9 Hz, 1H), 7.26 (m, 5H); [α]$_D^{25°}$ = −57.7° (0.1 M NaOH, c=0.39).

Anal. Calc'd. for C$_{19}$H$_{24}$N$_2$O$_5$S-H$_2$O; C, 55.59; H, 6.39; N, 6.83; S, 7.81. Found: C, 55.56; H, 6.45; N, 6.69; S, 7.90.

EXAMPLE 41

[3R[3α,6α(S*),9aα]]-6-[(1-Carboxy-3-phenylpropyl)amino]octahydro-1,1-dioxo-5-oxothiazolo[3,2-a]azepine-3-carboxylic acid To a solution of [3R-[3α,6α(S*),9aα]]-6-[(1-carboxy-3-phenylpropyl)amino]octahydro-5-oxothiazolo[3,2-a]azepine-3-carboxylic acid (0.1 mmole) in 1.2 ml of glacial acetic acid at 0°, a solution of KMnO$_4$ (0.014 mmole) in 1.2 ml of water can be added via a syringe pump over a period of two hours. The reaction mixture can be placed on a strong acid ion-exchange resin (Dowex 50 X-2) and eluted with water until eluant is near neutrality. The product can be recovered from the resin with 4% pyridine-water. The appropriate fraction can be freeze-dried to give crude sulfone which can be purified by chromatography on a reverse-phase column.

EXAMPLE 42

[3R-[3α,6α(S*),9aα]]-6-[(1-Carboxy-3-phenylpropyl)amino]octahydro-1,1-dioxo-5-oxothiazolo[3,2-a]azepine-3-carboxylic acid A solution of [3R-[3α,6α(S*),9aα]]-6-[(1- carboxy-3-phenylpropyl)amino]octahydro-5-oxothiazolo[3,2-a]azepine-3-carboxylic acid (50 mg) in glacial acetic acid (3 ml) can be stirred at 50°. A 30% solution of hydrogen peroxide (0.25 ml) can then be added slowly via a syringe pump over a period of 10 hours. The solution can be stirred at room temperature overnight, concentrated under reduced pressure and thoroughly dried to give the product.

EXAMPLE 43

3R-[3α,6α(S*),9aβ]]-6-[(1-Carboxy-3-phenylpropyl)amino]octahydro-1,1-dioxo-5-oxothiazolo[3,2-a]azepine-3-carboxylic acid A solution of [3R-[3α,6α(S*),9aβ]]-6-[(1-carboxy-3-phenylpropyl) amino]octahydro-5-oxothiazolo[3,2-a]azepine-3-carboxylic acid (100 mg) in glacial acetic acid (5 ml) can be stirred at 50°. A 30% solution of hydrogen peroxide (0.5 ml) can then be added slowly via a syringe pump over a period of 10 hours. The solution can be stirred at room temperature overnight. The solution can then be concentrated under reduced pressure and thoroughly dried to give the product.

EXAMPLE 44

Compressed Tablet containing 5 mg. of active ingredient

| | Per tablet, Mg. |
|---|---|
| [3R-[3α,6α(S*),9aβ]]-6-[(1-carboxy-3-phenylpropyl)amino]octahydro-1(R)-oxo-5-oxothiazolo[3,2-a]azepine-3-carboxylic acid | 5 |
| Calcium phosphate dibasic | 245 |
| Ethyl cellulose (as 5% solution in ethanol) | 5 |
| Unmixed granulation | 255 |
| Add: | |
| Starch, corn | 14 |
| Magnesium stearate | 1 |
| | 270 |

EXAMPLE 45

Dry filled capsule containing 5 mg. of active ingredient of Example 44.

| | Per capsule, mg. |
|---|---|
| Lactose | 5 |
| Magnesium stearate | 273 |
| Mixed powders | 2 |
| | 280 |

Mix the active ingredient above, lactose, and magnesium stearate and reduce to a No. 60 mesh powder. Encapsulate, filling 285 mg. in each No. 2 capsule.

EXAMPLE 46

Compressed Tablet containing 5 mg. of active ingredient

|  | Per tablet, Mg. |
|---|---|
| [3R-[3α,6α(S*),9aβ]]-6-[[1-(ethoxy-carbonyl)-3-phenylpropyl]amino]octahydro-1(R)-oxo-5-oxothiazolo[3,2-a]azepine-3-carboxylic acid | 5 |
| Calcium phosphate dibasic | 245 |
| Ethyl cellulose (as 5% solution in ethanol) | 5 |
| Unmixed granulation | 255 |
| Add: | |
| Starch, corn | 14 |
| Magnesium stearate | 1 |
|  | 270 |

EXAMPLE 47

Dry filled capsule containing 5 mg. of active ingredient of Example 46.

|  | Per capsule, mg. |
|---|---|
| Lactose | 5 |
| Magnesium stearate | 273 |
| Mixed powders | 2 |
|  | 280 |

Mix the active ingredient above, lactose, and magnesium stearate and reduce to a No. 60 mesh powder. Encapsulate, filling 285 mg. in each No. 2 capsule.

What is claimed is:

1. A compound of the formula:

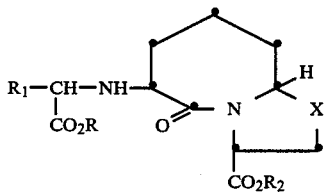

I wherein:

X is SO or $SO_2$;

R and $R_2$ are independently hydrogen, loweralkyl, aryl, and aralkyl;

$R_1$ is hydrogen;
  straight chain and branched alkyl of from 1 to 12 carbon atoms;
  $C_2$–$C_{12}$ straight chain and branched alkenyl and alkylnyl;
  cycloalkyl of 3 to 10 carbon atoms;
  substituted lower alkyl wherein the substituent can be halo, hydroxy, carboxy, lower alkylthio, lower alkoxy, lower alkoxy carbonyl, lower aralkoxy carbonyl, amino, lower alkylamino, lower dialkylamino, acetylamino or benzoylamino;
  substituted lower alkyl having the formula $R_A(CH_2)_n$—Q—$(CH_2)_m$ wherein n is 0–2, m is 1–3, $R_A$ is aryl or heteroaryl optionally substituted by amino, lower dialkylamino, lower alkylamino, hydroxy, loweralkyl, amino lower alkyl, trihaloloweralkyl, cyano, nitro, sulfonamido, benzoyl, 1-naphthoyl, lower alkyl, halo, dihalo, and lower alkoxy, and Q is O, S, N—$R_B$, $CONR_C$, $NR_CCO$, CH=CH wherein $R_B$ is hydrogen, lower alkyl, aryl, aralkyl, acetylamino, benzoylamino, benzoyl, or 1-naphthoyl, and $R_C$ is hydrogen or lower alkyl; aryl;
  substituted aryl wherein the substituent is lower alkyl, amino loweralkyl, loweralkoxy, aryloxy, benzoyl, 1-naphthoyl, hydroxy, halo, or dihalo; aralkyl or heteroaralkyl which include branched lower alkyl groups; substituted aralkyl or substituted heteroaralkyl which include branched lower alkyl groups wherein the lower alkyl groups can be substituted by amino, acetylamino, benzoylamino, or hydroxyl and the aryl and heteroaryl groups can be substituted by halo, dihalo, loweralkyl, hydroxy, loweralkoxy, aryloxy, benzoyl, 1-naphthoyl, arylthio, amino, amino lower alkyl, lower alkanoyl amino, aroylamino, lower dialkylamino, lower alkylamino, hydroxy, hydroxy loweralkyl, trihalo loweralkyl, nitro, cyano, or sulfonamido; and, the pharmaceutically acceptable salts thereof wherein in said R, $R_1$ and $R_2$ groups, unless otherwise indicated, the aralkyl and heteroalkyl groups have from one to six carbon atoms in the alkyl portion thereof; aryl and the prefix "ar" have 5–6 ring atoms; and, heteroaryl is a member selected from the groups consisting of, indolyl, thienyl, imidazolyl, furyl, benzimidazoylyl, pyridyl, quinolinyl, isoquinolinyl, and benzothienyl.

2. A compound of claim 1 wherein:

X is SO or $SO_2$;

R and $R_2$ are hydrogen, loweralkyl, aryl, or aralkyl; and, $R_1$ is alkyl of 1–10 carbon atoms which include branched, cyclic and unsaturated alkyl groups;
  substituted lower alkyl wherein the substituent can be hydroxy, lower alkylthio, amino, alkylamino, lower dialkylamino, and acylamino;
  substituted lower alkyl having the formula $R_A$ $(Ch_2)_n$—Q—$(CH_2)_m$—wherein n is 0–2, m is 1–3, $R_A$ is aryl or heteroaryl optionally substituted by alkyl, halo, dihalo, amino, cyano, hydroxy, or alkoxy, and Q is O, S, N—$R_B$, $CONR_C$, $NR_CCO$, or CH=CH, wherein $R_B$ is hydrogen, lower alkyl, aralkyl, lower alkanoyl, or aroyl and $R_C$ is hydrogen or lower alkyl; aralkyl or heteroaralkyl which include branched lower alkyl groups;
  substituted aralkyl or substituted heteroaralkyl which include branched lower alkyl groups wherein the lower alkyl substituents can be amino, acylamino, or hydroxy and the aryl and heteroaryl substituents can be lower alkyl, halo, dihalo, amino, cyano, hydroxy, lower alkoxy, amino loweralkyl, or hydroxyloweralkyl.

3. A compound of claim 1 wherein:

X is SO or $SO_2$;

R and $R_2$ are independently hydrogen, loweralkyl, aryl, or aralkyl; and $R_1$ is alkyl of 1–10 carbon atoms which include branched alkyl groups;
  substituted lower alkyl wherein the substituent can be amino, acylamino, or lower alkylthio;
  substituted lower alkyl having the formula $R_A(CH_2)_n$—Q—$(CH_2)_m$— wherein n is 0–1, m is 1–2, $R_A$ is phenyl optionally substituted by halo, dihalo, alkoxy, or cyano, and Q is O or S; aralkyl or heteroaralkyl;
  substituted aralkyl or substituted heteroaralkyl wherein the aryl and heteroaryl substituents are halo, dihalo, cyano, hydroxy, hydroxy lower alkyl, amino, and amino lower alkyl.

4. A compound of claim 1 wherein:

X is SO or $SO_2$;

R and $R_2$ are independently hydrogen, lower alkyl of 1 to 4 carbon atoms, phenyl, or benzyl; and, $R_1$ is alkyl of 1-8 carbon atoms which include branched alkyl groups;

substituted lower alkyl wherein the substituent can be amino or loweralkylthio;

substituted lower alkyl having the formula $R_A(CH_2)_n$—Q—$(CH_2)_m$— wherein n is 0, m is 1, $R_A$ is phenyl, and Q is O or S; aralkyl wherein the aryl is phenyl or naphthyl and the alkyl group contains 1 to 3 carbon atoms, or heteroaralkyl wherein the heteroaryl group is indole, thiophene, imidazole, pyridine, quinoline or isoquinoline and the alkyl group contains 1 to 3 carbon atoms;

substituted aralkyl wherein the aryl is a phenyl group, the alkyl contains 1 to 3 carbon atoms, and the phenyl substituents can be halo, hydroxy, phenoxy, lower alkoxy, amino, or aminomethyl.

5. A compound of claim 4 having the formula:

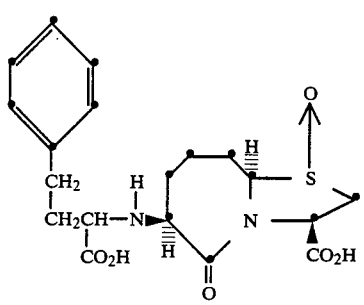

6. The compound of claim 5 which is: [3R-[3α,-6α(S*),9aβ]]-6-[(1-carboxy-3-phenylpropyl)amino]octahydro-1(R)-oxo-5-oxothiazolo[3,2-a]azepine-3-carboxylic acid.

7. A compound of claim 4 having the formula:

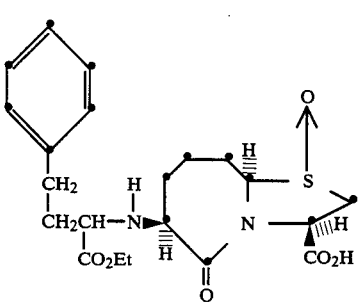

8. The compound of claim 7 which is: [3R-[3α,-6α(S*),9a β]]-6-[[1-ethoxycarbonyl-3-phenylpropyl]amino]octahydro-1(R)-oxo-5-oxothiazolo [3,2-a]azepine-3-carboxylic acid.

9. A compound of claim 4 having the formula:

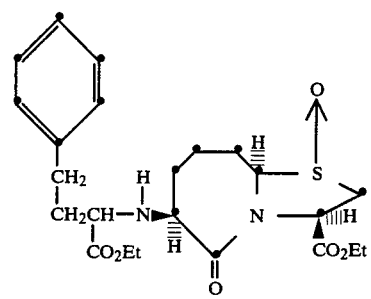

10. The compound of claim 9 which is: Ethyl [3R-[3α,6α(S*),9 aβ]]-6-[[1-(ethoxycarbonyl)-3-phenylpropyl]amino]octahydro-1(R)-oxo-5-oxothiazolo[3,2-a]azepine-3-carboxylate.

11. A compound of claim 4 having the formula:

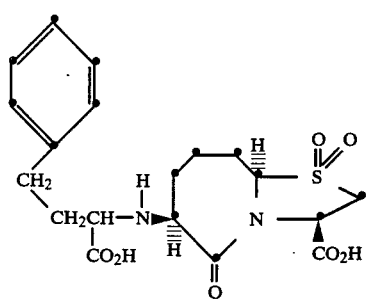

12. The compound of claim 11 which is: [3R-[3α,-6α(S*),9aβ]]-6-[(1-carboxy-3-phenylpropyl) amino]octahydro-1,1-dioxo-5-oxothiazolo[3,2-a]azepine-3-carboxylic acid.

13. A compound of claim 4 having the formula:

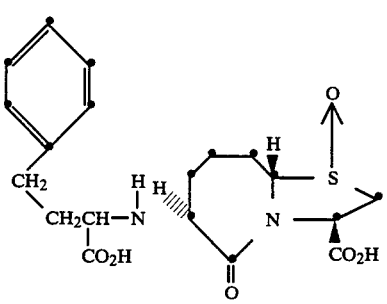

14. The compound of claim 13 which is: [3R-[3α,-6α(S*), 9aα]]-6-[(1-carboxy-3-phenylpropyl) amino]octahydro-1(S)-oxo-5-oxothiazolo[3,2-a]azepine-3-carboxylic acid.

15. A compound of claim 4 having the formula:

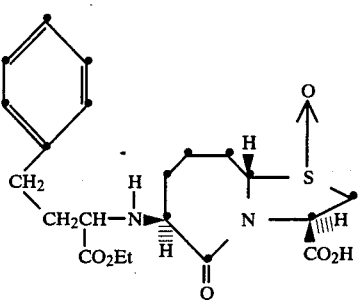

16. The compound of claim 15 which is: [3R-[3α,-6α(S*),9aα]]-6-[[1-ethoxycarbonyl)-3-phenylpropyl-]amino]octahydro-1(S)-oxo-5-oxothiazolo[3,2-a]-azepine-3-carboxylic acid.

17. A pharmaceutical composition useful in the treatment of hypertension which comprises a pharmaceutically acceptable carrier and a pharmaceutically effective amount of a compound of the formula:

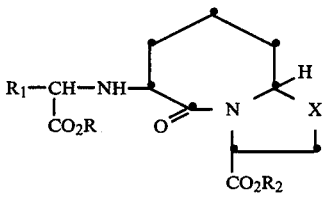

wherein:

X is SO or $SO_2$;

R and $R_2$ are independently hydrogen, loweralkyl, aryl, and aralkyl;

$R_1$ is hydrogen straight chain and branched alkyl of from 1 to 12 carbon atoms;

$C_2$-$C_{12}$ straight chain and branched alkenyl and alkylnyl;

cycloalkyl of 3 to 10 carbon atoms;

substituted lower alkyl wherein the substituent can be halo, hydroxy, carboxy, lower alkylthio, lower alkoxy, lower alkoxy carbonyl, lower aralkoxy carbonyl, amino, lower alkylamino, lower dialkylamino, acetylamino, or benzoylamino;

substituted lower alkyl having the formula $R_A(CH_2$-$)_n$—Q—$(CH_2)_m$ wherein n is 0-2, m is 1-3, $R_A$ is aryl or heteroaryl optionally substituted by amino, lower dialkylamino, lower alkylamino, hydroxy, hydroxy loweralkyl, amino lower alkyl, trihalo loweralkyl, cyano, nitro, sulfonamido, benzoyl, 1-naphthoyl, lower alkyl, halo, dihalo, and lower alkoxy, and Q is O, S, N—$R_B$, $CONR_C$, $NR_CCO$, CH=CH whrein $R_B$ is hydrogen, lower alkyl, aryl, aralkyl, acetylamino, benzoylamino, benzoyl, or 1-naphthoyl, and $R_C$ is hydrogen or lower alkyl; aryl;

substituted aryl wherein the substituent is lower alkyl, amino loweralkyl, loweralkoxy, aryloxy, benzoyl, 1-naphthoyl, hydroxy, halo, or dihalo; aralkyl or heteroaralkyl which include branched lower alkyl groups;

substituted aralkyl or substituted heteroaralkyl which include branched lower alkyl groups wherein the lower alkyl groups can be substituted by amino, acetylamino, benzoylamino or hydroxyl and the aryl and heteroaryl groups can be substituted by halo, dihalo, loweralkyl, hydroxy, loweralkoxy, aryloxy, benzoyl, 1-naphthoyl, arylthio, amino, amino lower alkyl, lower alkanoyl amino, aroylamino, lower dialkylamino, lower alkylamino, hydroxy, hydroxy loweralkyl, trihalo loweralkyl, nitro, cyano, or sulfonamido; and, the pharmaceutically acceptable salts thereof wherein in said R, $R_1$ and $R_2$ groups, unless otherwise indicated, the aralkyl and heteroaralkyl groups have from one to six carbon atoms in the alkyl portion thereof; aryl and the prefix "ar" have 5-6 ring atoms; and, heteroaryl is a member selected from the groups consisting of, indolyl, thienyl, imidazolyl, furyl, benizimidazolyl, pyridyl, quinolinyl, isoquinolinyl, and benzothienyl.

18. The composition of claim 17 wherein the said pharmaceutically effective compound is a member of the group:

[3R-[3α, 6α(S*),9aβ]]-6-[(1-carboxy-3-phenylpropyl) amino]-octahydro-1(R)-oxo-5-oxothiazolo[3,2-a]-azepine-3-carboxylic acid;

[3R-[3α6α(S*),9aβ]]-6-[[1-(ethoxycarbonyl)-3-phenyl-propyl]amino]octahydro-1(R)-oxo-5-oxothiazolo[3,2-a]azepine-3-carboxylic acid;

Ethyl [3R-[3α, 6α(S*),9aβ]]-6-[[1-(ethoxycarbonyl)-3-phenylpropyl]amino]octahydro-1(R)-oxo-5-oxo-thiazolo[3,2-a]azepine-3-carboxylate;

[3R-[3α6α(S*),9aβ]]-6-[(1-carboxy-33-phenylpropyl) amino]octahydro-1,1-dioxo-5-oxothiazolo[3,2-a]-azepine-3-carboxylic acid;

3R-[3α,6α(S*),9aα]]-6-[(1-carboxy-3-phenylpropyl) amino]octahydro-1(S)-oxo-5-oxothiazolo[3,2-a]-azepine-3-carboxylic acid;

[3R-[3α,6α(S*), 9aα]]--6-[[1-(ethoxycarbonyl)-3-phenylpropyl]amino]oc-tahydro-1(S)-oxo-5-oxothiazolo[3,2-a]azepine-3-carboxylic acid.

19. The composition of Claim 17 which includes another antihypertensive and/or diuretic compound selected from the group amiloride, atenolol, bendroflumethiazide, chlorothalidone, chlorothiazide, clonidine, cryptenamine acetate and cryptenamine tannates, deserpidine, diazoxide, ethacrynic acid, furosemide, guanethidene sulfate, hydralazine hydrochloride, hydrochlorothiazide, hydroflumethiazide, metolazone, metoprolol tartate, methyclothiazide, methyldopa, methyldopate hydrochloride, minoxidil, (S)-1-{[2-(3,4-dimethoxyphenyl)ethyl]amino}-3-{[4-(2-thienyl)-1H-imidazol-2-yl]phenoxy}-2-propanol, polythiazide, the pivaloyloxyethyl ester of methyldopa, indàcrinone and variable ratios of its enantiomers, nifedipine, verapamil, diltiazam, flumethiazide, bendroflumethiazide, atenolol, (+)-4-{3-[2-(1-hydroxycyclohexyl)ethyl]-4-oxo-2-thiazolidinyl]propyl}benzoic acid, bumetanide, prazosin, propranolol, *rauwolfia serpentina*, rescinnamine, reserpine, spironolactone, timolol, trichlormethiazide, benzthiazide, quinethazone, tricrynafan, triamterene, acetazolamide, aminophylline, cyclothiazide, merethoxylline procaine, and the like, as well as admixtures and combinations thereof.

20. A method for treating hypertension which comprises administering to a patient in need of such treatment a pharmaceutically effective amount of a compound of the formula:

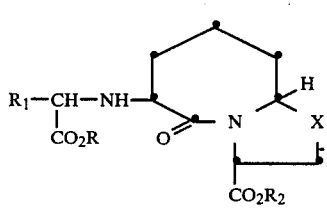

wherein:

X is SO or SO$_2$;

R and R$_2$ are independently hydrogen, loweralkyl, aryl, and aralkyl;

R$_1$ is hydrogen;

straight chain and branched alkyl of from 1 to 12 carbon atoms;

C$_2$-C$_{12}$ straight chain and branched alkenyl and alkynyl;

cycloalkyl of 3 to 10 carbon atoms;

substituted lower alkyl wherein the substituent can be halo, hydroxy, carboxy, lower alkylthio, lower alkoxy, lower alkoxy carbonyl, lower aralkoxy carbonyl, amino, lower alkylamino, lower dialkylamino, acetylamino, or benzoylamino;

substituted lower alkyl having the formula R$_A$(CH$_2$)$_n$—Q—(CH$_2$)$_m$ wherein n is 0-2, m is 1-3, R$_A$ is aryl or heteroaryl optionally substituted by amino, lower dialkylamino, lower alkylamino, hydroxy, hydroxy loweralkyl, amino lower alkyl, trihalo loweralkyl, cyano, nitro, sulfonamido, benzoyl, 1-naphthoyl, lower alkyl, halo, dihalo, and lower alkoxy, and Q is O, S, N—R$_B$, CONR$_C$, NR$_C$CO, CH=CH wherein R$_B$ is hydrogen, lower alkyl, aryl, aralkyl, acetylamino, benzoylamino, benzoyl, or 1-naphthoyl, and R$_C$ is hydrogen or lower alkyl; aryl;

substituted aryl wherein the substituent is lower alkyl, amino loweralkyl, loweralkoxy, aryloxy, benzoyl, 1-naphthoyl, hydroxy, halo, or dihalo; aralkyl or heteroaralkyl which include branched lower alkyl groups;

substituted aralkyl or substituted heteroaralkyl which include branched lower alkyl groups wherein the lower alkyl groups can be substituted by amino, acetylamino, benzoylamino, or hydroxyl and the aryl and heteroaryl groups can be substituted by halo, dihalo, loweralkyl, hydroxy, loweralkoxy, aryloxy, benzoyl, 1-naphthoyl, arylthio, amino, amino lower alkyl, lower alkanoylamino, aroyl amino, lower dialkylamino, lower alkylamino, hydroxy, hydroxy loweralkyl, trihalo loweralkyl, nitro, cyano, or sulfonamido; and, the pharmaceutically acceptable salts thereof wherein in said R, R$_1$ and R$_2$ groups, unless otherwise indicated, the aralkyl and heteroaralkyl groups have from one to six carbon atoms in the alkyl portion thereof; aryl and the prefix "ar" have 5-6 ring atoms; and, heteroaryl is a member selected from the groups consisting of, indolyl, thienyl, imidazolyl, furyl, benzimidazolyl, pyridyl, quinolinyl, isoquinolinyl, and benzothienyl.

21. A process for producing compounds having the formula:

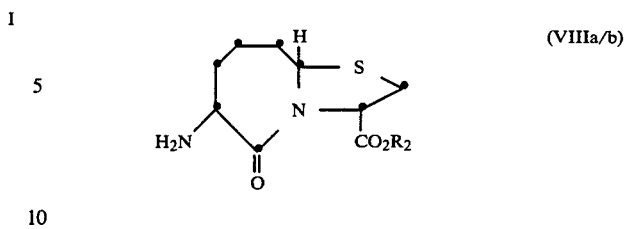

wherein R$_2$ is as defined in claim 1.

which comprise:

reacting a compound having the formula:

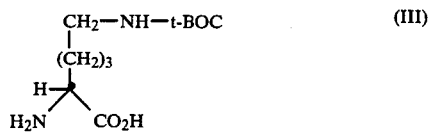

with carbethoxyphthalamide and then trifluoroacetic acid to obtain a compound having the formula:

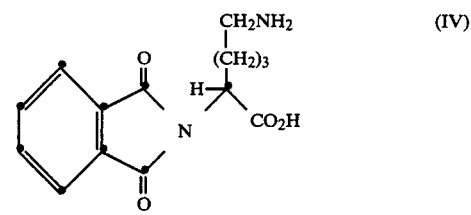

condensing said formula IV compound with 4-formyl-1- methylpyridinium benzenesulfonate to obtain a Schiff base;

equilibrating said Schiff base with 1,8-diazabicyclo[5.4.0]undec-7-ene (DBU) to obtain a compound having the formula:

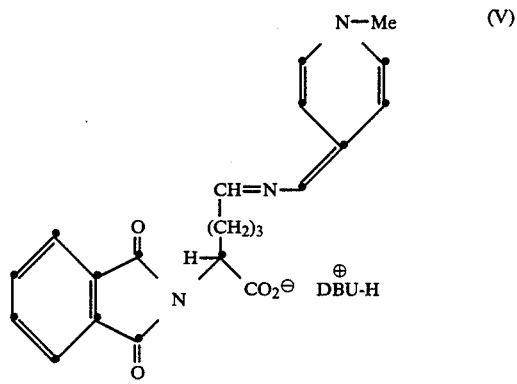

adding an ester of R-cysteine hydrochloride to said formula V compound to obtain compounds having the formula:

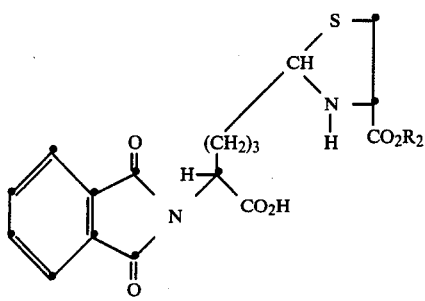 (VI)

treating said formula VI compound with N-ethoxy-carbonyl-2-ethoxy-1,2-dihydroquinoline or N-isobutoxycarbonyl-2-isobutoxy-1,2-dihydroquinoline to obtain compounds having the formula:

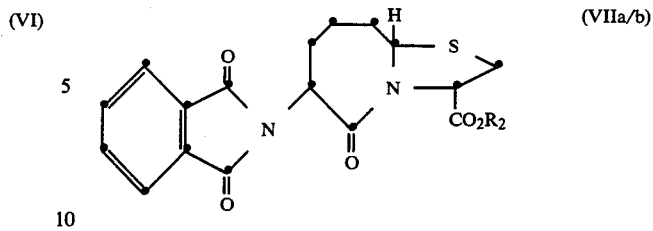 (VIIa/b)

reacting said formula VIIa/b compounds with hydrazine to obtain said formula VIIIa/b compounds as a diastereomeric mixture; and, if desired, separating said diastereomeric mixture to obtain the separate diastereomeric compounds; or, if desired, converting said formula VIIIb compound to said formula VIIIa compound by means of acid equilibration.

* * * * *